(12) United States Patent
Bortone

(10) Patent No.: US 11,622,873 B2
(45) Date of Patent: Apr. 11, 2023

(54) MULTILAYER LUMINAL ENDOPROSTHESIS ASSEMBLY AND MANUFACTURING METHOD

(71) Applicant: DYVERTO AG, Zug (CH)

(72) Inventor: Alessandro Santo Bortone, Bari (IT)

(73) Assignee: Dyverto AG, Zug (CH)

( * ) Notice: Subject to any disclaimer, the term of this patent is extended or adjusted under 35 U.S.C. 154(b) by 722 days.

(21) Appl. No.: 16/489,969

(22) PCT Filed: Mar. 6, 2018

(86) PCT No.: PCT/IB2018/051425
§ 371 (c)(1),
(2) Date: Aug. 29, 2019

(87) PCT Pub. No.: WO2018/163056
PCT Pub. Date: Sep. 13, 2018

(65) Prior Publication Data
US 2019/0388251 A1 Dec. 26, 2019

(30) Foreign Application Priority Data

Mar. 6, 2017 (IT) .................. 102017000024729
Mar. 6, 2017 (IT) .................. 102017000024763

(51) Int. Cl.
*A61F 2/90* (2013.01)
*A61F 2/848* (2013.01)
(Continued)

(52) U.S. Cl.
CPC .................. *A61F 2/90* (2013.01); *A61F 2/04* (2013.01); *A61F 2/848* (2013.01); *A61F 2/852* (2013.01);
(Continued)

(58) Field of Classification Search
CPC .............. A61F 2/852; A61F 2210/0076; A61F 2250/0039
See application file for complete search history.

(56) References Cited

U.S. PATENT DOCUMENTS 5,354,309 A 10/1994 Schnepp-Pesch et al.
5,718,159 A 2/1998 Thompson
(Continued)

FOREIGN PATENT DOCUMENTS

BR 202013033688 U2 11/2015
EP 1 357 857 B1 5/2007
(Continued)

OTHER PUBLICATIONS

Japanese Office Action for Japanese Patent Application No. 2019-547990 dated Nov. 2, 2021, 19 pages.
(Continued)

*Primary Examiner* — Rebecca S Preston
(74) *Attorney, Agent, or Firm* — Merchant & Gould P.C.

(57) ABSTRACT

A luminal endoprosthesis assembly (1) at least partially delimits a prosthesis lumen (2), for implantation in an anatomical structure (3) that at least partially defines at least one cavity (4) and includes at least one pathological portion (13). The luminal endoprosthesis (1) has two or more layers (5, 6, 7). At least one layer (5, 6, 7) includes a threadlike element (8) forming an armor (9). The luminal endoprosthesis (1) includes an anchoring portion (10) for anchoring to an anatomical portion (11) of the walls of the cavity (4) of the anatomical structure (3), and a working portion (12) for facing the pathological portion (13) of the anatomical structure (3). The two or more layers (5, 6, 7) are separated from each other in the working portion (12) of the luminal endoprosthesis (1), avoiding connecting elements between one layer (5, 6, 7) and at least one adjacent layer.

19 Claims, 20 Drawing Sheets

(51) Int. Cl.
  *A61F 2/852* (2013.01)
  *A61F 2/04* (2013.01)
  *B21F 27/12* (2006.01)
  *A61F 2/86* (2013.01)
  *A61F 2/82* (2013.01)

(52) U.S. Cl.
  CPC .............. *A61F 2/86* (2013.01); *B21F 27/121* (2013.01); *A61F 2002/044* (2013.01); *A61F 2002/823* (2013.01); *A61F 2002/8486* (2013.01); *A61F 2210/0004* (2013.01); *A61F 2210/0014* (2013.01); *A61F 2210/0076* (2013.01); *A61F 2220/0025* (2013.01); *A61F 2220/0058* (2013.01); *A61F 2220/0075* (2013.01); *A61F 2230/001* (2013.01); *A61F 2230/0067* (2013.01); *A61F 2240/001* (2013.01); *A61F 2250/0003* (2013.01); *A61F 2250/0008* (2013.01); *A61F 2250/0039* (2013.01); *A61F 2250/0098* (2013.01)

(56) References Cited

U.S. PATENT DOCUMENTS

| | | | |
|---|---|---|---|
| 6,165,209 A | 12/2000 | Patterson et al. | |
| 6,689,162 B1 | 2/2004 | Thompson | |
| 8,048,139 B2 | 11/2011 | Frid et al. | |
| 8,192,484 B2 | 6/2012 | Frid | |
| 2008/0262593 A1* | 10/2008 | Ryan | A61F 2/90 623/1.12 |
| 2009/0270974 A1 | 10/2009 | Berez et al. | |
| 2013/0218255 A1 | 8/2013 | Cattaneo et al. | |
| 2013/0245745 A1 | 9/2013 | Vong et al. | |
| 2014/0180392 A1 | 6/2014 | Shoham et al. | |
| 2015/0216684 A1 | 8/2015 | Enzmann et al. | |
| 2015/0282967 A1 | 10/2015 | Beard et al. | |
| 2016/0158037 A1 | 6/2016 | Shin et al. | |
| 2018/0064525 A1* | 3/2018 | Frid | A61F 2/2412 |
| 2018/0070955 A1* | 3/2018 | Greene, Jr. | A61B 17/12109 |
| 2019/0183667 A1* | 6/2019 | Park | B33Y 70/00 |

FOREIGN PATENT DOCUMENTS

| | | |
|---|---|---|
| EP | 1 946 721 A1 | 7/2008 |
| EP | 2 397 112 A1 | 12/2011 |
| KR | 2016-0133388 A | 11/2016 |
| WO | 90/04982 A1 | 5/1990 |
| WO | 2016/124235 A1 | 8/2016 |

OTHER PUBLICATIONS

International Search Report and Written Opinion of the International Searching Authority for International Patent Application No. PCT/IB2018/051425 dated May 18, 2018, 9 pages.

\* cited by examiner

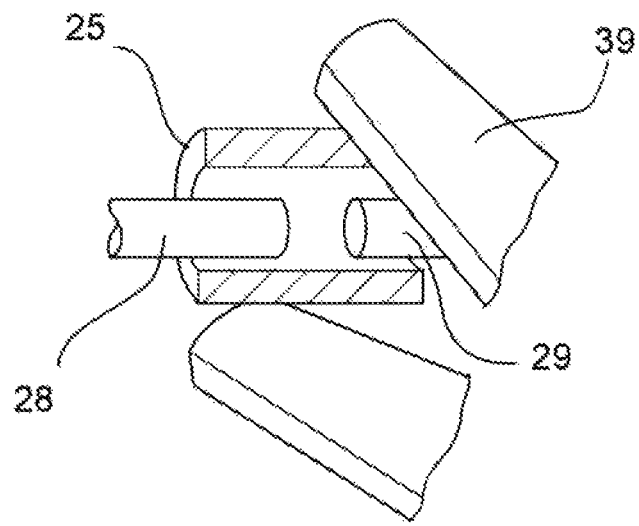
FIG. 21
FIG. 22
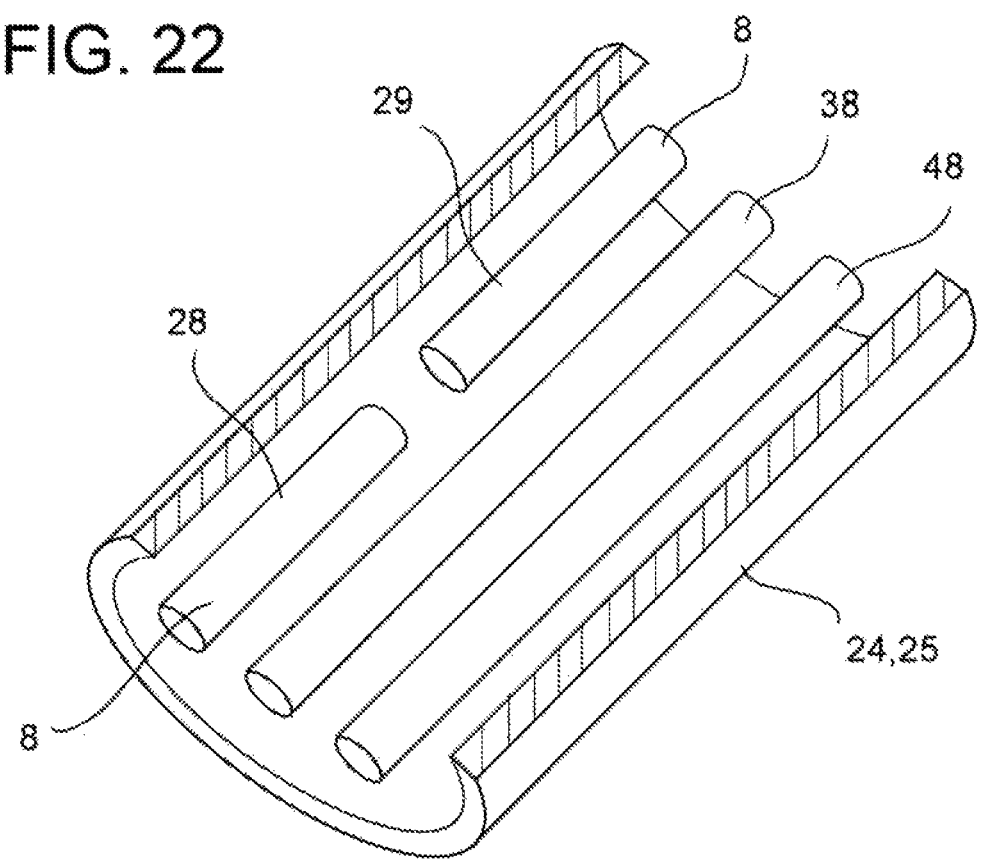

MULTILAYER LUMINAL ENDOPROSTHESIS ASSEMBLY AND MANUFACTURING METHOD

This application is a National Stage Application of PCT/IB2018/051425, filed 6 Mar. 2018, which claims benefit of Ser. No. 10/217,000024729, filed 6 Mar. 2017 in Italy and Serial No. 102017000024763, filed 6 Mar. 2017 in Italy, and which applications are incorporated herein by reference. To the extent appropriate, a claim of priority is made to each of the above-disclosed applications.

FIELD OF THE INVENTION

The present invention relates to a luminal endoprosthesis assembly.

In particular, the present invention relates to a multilayer luminal endoprosthesis.

An endoprosthesis according to the present invention is particularly suitable, but not univocally intended, for the treatment of aneurysms.

BACKGROUND ART

Luminal endoprostheses are used for the treatment of cardiovascular diseases such as aneurysms. An aneurysm substantially consists of a pathological dilation of the section of a portion of a blood vessel, for example an artery such as the aorta, which is the main artery of the cardiovascular system, to form a sac called aneurysmal sac. From the hemodynamic point of view, the blood stream at such a dilation of the passage section tends to flow in turbulent regime and at the same time to exert a pressure of increased intensity on the walls of the blood vessel compared to that which is found in healthy blood vessels. This causes an unstoppable increase in the section of the vessel which corresponds to a reduction in the thickness of the wall thus causing, according to Laplace's law, a chronic expansion of the aneurysmal sac which can lead to the rupture of the vessel wall.

In particular, a wall tension develops in the aneurysmal sac, at equal pressure, higher than that of the healthy vessel, which by the Laplace law is twice inversely proportional to the radius of the sac, and the flow, which is turbulent rather than laminar, has a whirling effect which creates an inflow of blood from the vessels surrounding the aneurysmal sac as well as a laminar flow from the aorta to the neighboring vessels. This over-expands the aneurysmal dilatation leading to the rupture of the aorta due to the vascular tension no longer contained by the external tunica adventitia, since the muscle-elastic tunica media is already degenerated and therefore has given rise to the aneurysmal dilation itself.

By the implantation of a luminal endoprosthesis in a blood vessel, it is possible to locally influence the fluid dynamics inside the vessel and it is therefore possible to reduce the turbulence of the blood stream. This phenomenon is known as flow diversion. Due to the known structural features, luminal endoprostheses are able to channel the blood stream excluding it from the aneurysmal sac. In this way, the transport phenomena within the sac due to the blood stream are substantially eliminated and at the same time, the stress imparted by the blood on the walls of the aneurysmal sac is reduced, thus preventing the rupture of the sac walls and leading to a progressive filling of the aneurysmal sac with clots of blood.

Known luminal endoprosthesis usually include a release system for the insertion and positioning of the endoprosthesis in the lumen of the blood vessel astride of the inlet collar of the aneurysmal sac, a self-expanding metal armor (stent) capable of anchoring itself by pressing against the walls of the blood vessel affected by the aneurysm, a tissue (graft) to form the endoprosthesis wall to reconstruct a duct for the blood stream astride of the inlet collar of the aneurysmal sac which excludes the aneurysm. Endoprostheses of this type are described for example by documents EP-2397112 and US-2015-282967.

Known types of endoprostheses can be variously shaped. For example, from documents WO-90-04982 and U.S. Pat. No. 5,354,309, endoprostheses are known having proximal and distal ends of greater caliber than the central portion of the endoprosthesis. Endoprostheses can be manufactured by laser cutting of the stitches starting from sheets of shape-memory alloys or by means of a plurality of metal or polymeric threads around a spindle, as described for example by document U.S. Pat. No. 5,718,159.

Luminal endoprostheses are intended to remain implanted within blood vessels, usually arteries, such as the aorta, which are subjected to a pulsatile flow regime during the cardiac cycle and usually include deformable blood vessel walls which describe a curved and sometimes tortuous path. This phenomenon is particularly relevant for the treatment of aneurysms of the descending stretch of the aorta, i.e. the portion of the aorta artery distal to the aortic arch and comprising the aortic isthmus, the thoracic aorta, and the abdominal aorta and collateral blood vessels that branch off it. The blood stream of the aorta, being the artery in which the blood coming out of the left heart is conveyed, may be affected in normal physiological conditions by turbulent phenomena and is usually characterized by a substantially spiral advancement motion, which correspondingly causes the alignment of the endothelial cells of the aorta wall in an inclined direction with respect to the longitudinal direction of development of the vessel.

The wall of the arteries includes three layers: the adventitial tunica, which is the outermost layer fed by the so-called "vasa vasorum", the tunica media, formed by muscle-elastic fibers to exploit the elastic return to the nominal diameter following the expansion due to the systolic wave in order to promote blood circulation, and the tunica intima, which is the innermost layer suitable for promoting the diffusion of nutrients between the lumen and the tunica media. Thus, during the cardiac cycle, the artery wall is usually subjected to cycles of expansion and contraction of its nominal diameter, as well as flexion-torsional deformations in the three dimensions of the space.

For example, documents U.S. Pat. No. 8,192,484, EP-1357857 and U.S. Pat. No. 8,048,139 describe luminal endoprosthesis solutions comprising only an interleaved multilayer metal armor where each layer is formed by the interleaving of a plurality of metal filaments, and where filaments of each layer intersect with the filaments of adjacent layers causing a widespread integration or interpenetration between the various layers of the armor of the endoprosthesis.

Although advantageous from some points of view and particularly in the ability of locally reducing the turbulence of the blood stream, these solutions have quite a few drawbacks and do not fully solve the problem.

In fact, while the multilayer construction is capable of increasing the radial pressure that the stent exerts on the inner walls of the blood vessel, such a construction having interpenetrated layers is extremely rigid and therefore unsuitable for effectively adhering to the walls of a curved or "compliant" portion of the blood vessel. In other words, the implantation of a rigid structure, the endoprosthesis, in a pulsatile and compliant system, the large artery, necessarily generates an incompatibility that results in poor adherence of the endoprosthesis to the artery walls, at least in the first period following implantation, with the risk of early implant failure and undesired endoprosthesis migration.

In addition, the interpenetrated layers of such endoprosthesis solutions, when they successfully achieve anchoring, become an ideal substrate for the regeneration of vascular endothelial cells of the artery wall, with the result that the layers are incorporated into the wall of the artery, and often also the layers of the endoprosthesis portion facing the aneurysmal sac, are incorporated into the artery wall, thus excluding the aneurysmal sac from the blood stream and also occluding the collateral vessels branching off the artery at the implant site. In some sporadic cases, the growth of vascular endothelial cells on the armor of the endoprosthesis may fortunately avoid covering the entire portion of the endoprosthesis facing the aneurysmal sac, maintaining the patency of the collateral vessels, particularly if large caliber.

Other endoprosthesis solutions are known from WO2016124235A1, US 2016/0158037, EP1946721 A1, US 2015/216684, US 2013/218255, US 2013/245745, US 2009/270974, U.S. Pat. No. 6,689,162 and BR202013033688-U2 and KR20160133388.

In particular, the solutions so far proposed create a mismatch between the vessel wall and the flow as they are formed by interleaved and rigid multi-stent systems that do not conform to the optimal transmission of the flexion-torsional forces and therefore fail to re-establish a laminar flow, the absence of the inevitably leads to thrombosis and to the lack of perfusion of collateral vessels.

The need to provide a luminal endoprosthesis solution capable of adhering to the walls of the blood vessel in which it is implanted also during the physiological deformations of the vessel is therefore strongly felt.

Furthermore, the need is felt to provide a luminal endoprosthesis solution capable of providing a diversion of the blood flow, greatly reducing the turbulence thereof and at the same time capable of maintaining the patency of the collateral blood vessels branching off the vessel in which the luminal endoprosthesis is implanted in a controlled and predictable manner.

Known luminal endoprostheses of the type described above form a barrier which substantially encapsulates the pathological portion of the blood vessel, for example the aneurysm, and isolates it from the blood stream which is conveyed into the lumen of the endoprosthesis. From the clinical point of view, the effect of these endoprostheses is to promote the accumulation of blood clots, or thrombi, inside the aneurysmal sac.

Therefore, the known luminal endoprosthesis solutions do not clearly recognize the need to provide a luminal endoprosthesis solution capable of promoting the progressive recovery of the blood vessel function affected by pathological conditions, such as an aneurysm.

At the same time, the need to restore the response of a healthy wall through the implantation of a luminal endoprosthesis is felt.

Furthermore, the need to restore the dynamic and structural behavior of the blood vessel wall affected by the pathological condition is strongly felt in order to intervene where the structure and dynamics of the vessel has been compromised, recovering it.

Solution

It is an object of the present invention to obviate the drawbacks of the prior art mentioned above and to provide a solution to the requirements mentioned with reference to the prior art.

This and other objects are achieved by an endoprosthesis assembly according to claim 1.

Some advantageous embodiments are the subject of the dependent claims.

According to an aspect of the invention, a luminal endoprosthesis, at least partially delimiting a prosthesis lumen, is suitable for the implant in an anatomical structure that at least partially defines at least one cavity, forming at least one pathological portion. This luminal endoprosthesis comprises two or more endoprosthesis layers. At least one layer of said two or more layers comprises at least one filiform element or threadlike element forming an framework or armor.

Said luminal endoprosthesis comprises at least one anchoring portion, suitable for being anchored to an anatomical portion of the walls of the cavity of the anatomical structure, and at least one working portion, suitable for facing towards the pathological portion of the anatomical structure.

Advantageously, said two or more layers are separated from each other at least in said working portion of the luminal endoprosthesis, thus avoiding to provide connecting elements between one layer (5 or 6 or 7) and at least one adjacent layer.

The multilayer luminal endoprosthesis or device has the advantage of being conformable or extremely flexible and therefore of being able to be implanted in any type of vessel curvature. Its architecture is such as to return a new tunica media and then to restore and transmit in an optimal manner the normal flexion-torsional forces, with a normal sliding of the layers, for example of the three layers of which it is made in the three spatial axes, and thus re-establish the laminar flows not only in the aorta but also in the collateral vessels that branch off it without thrombosis neither of the device nor of the aneurysmal sac, which will therefore undergo a depressurization and therefore an effect of reabsorption and fibrosis of the aneurysm, called shrinkage, with an endothelialization of the spin-shape device that allows the laminar flow in all collateral vessels and the normal endocrine and antithrombotic function of the endothelium itself.

FIGURES

Further features and advantages of the endoprosthesis and of the method according to the invention will be readily apparent from the following description of preferred embodiment examples thereof, provided purely by way of a non-limiting example, with reference to the accompanying figures, in which.

Figure 1:
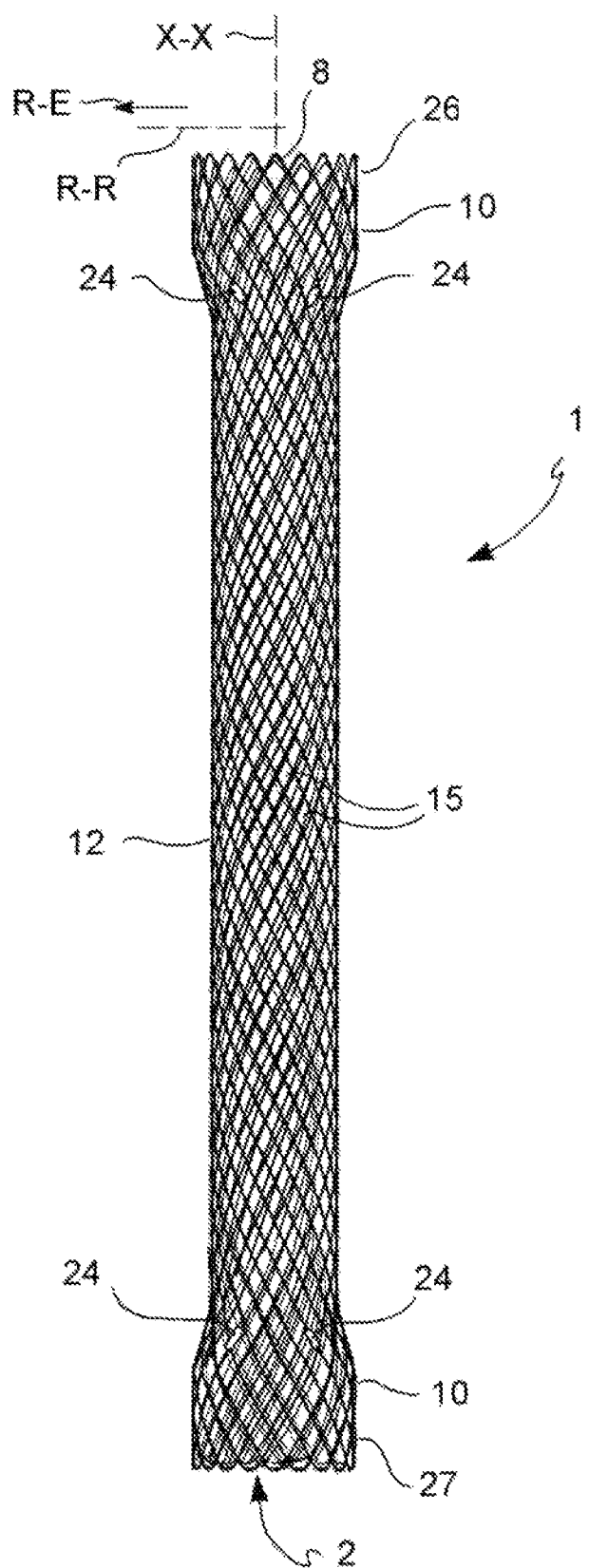
FIG. 1 shows a lateral or vertical elevation view of a luminal endoprosthesis.
Figure 2A:
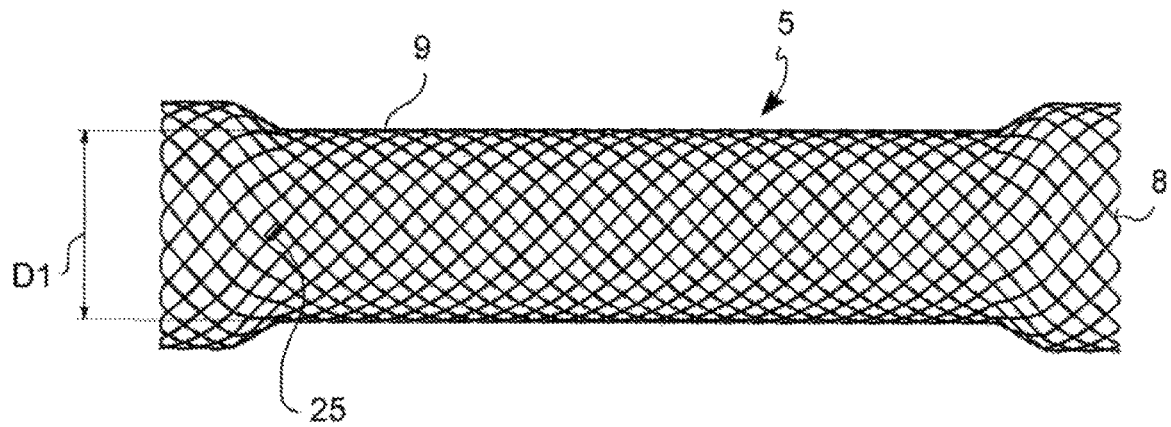
FIGS. 2A, 2B and 2C show each a vertical elevation view of a layer of a multilayer endoluminal prosthesis.
Figure 2B:
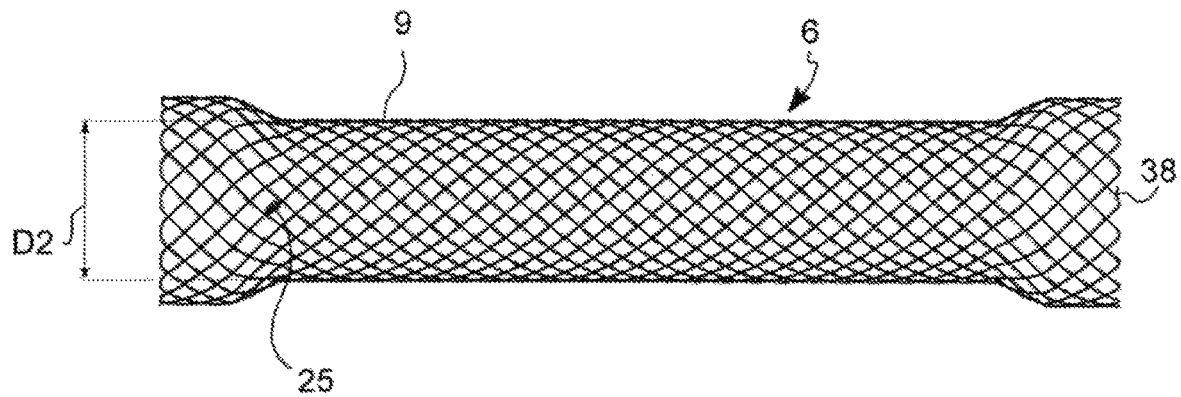
Figure 2C:
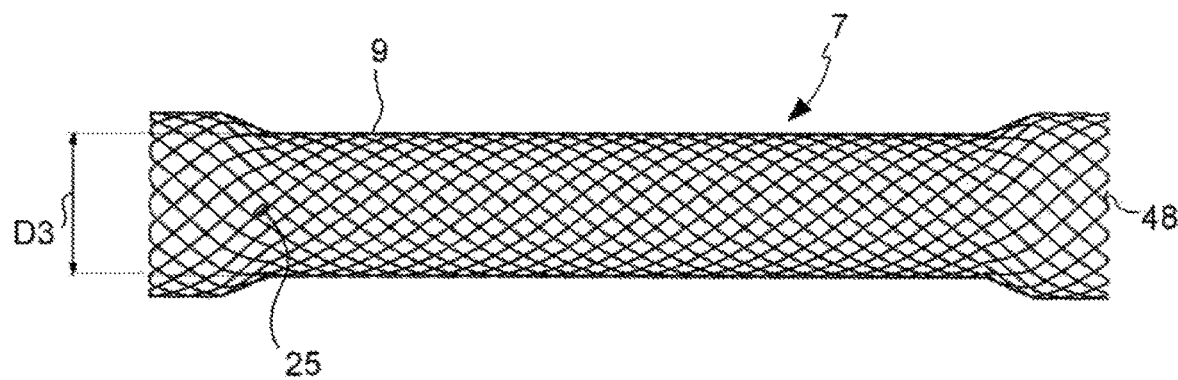
Figure 3:
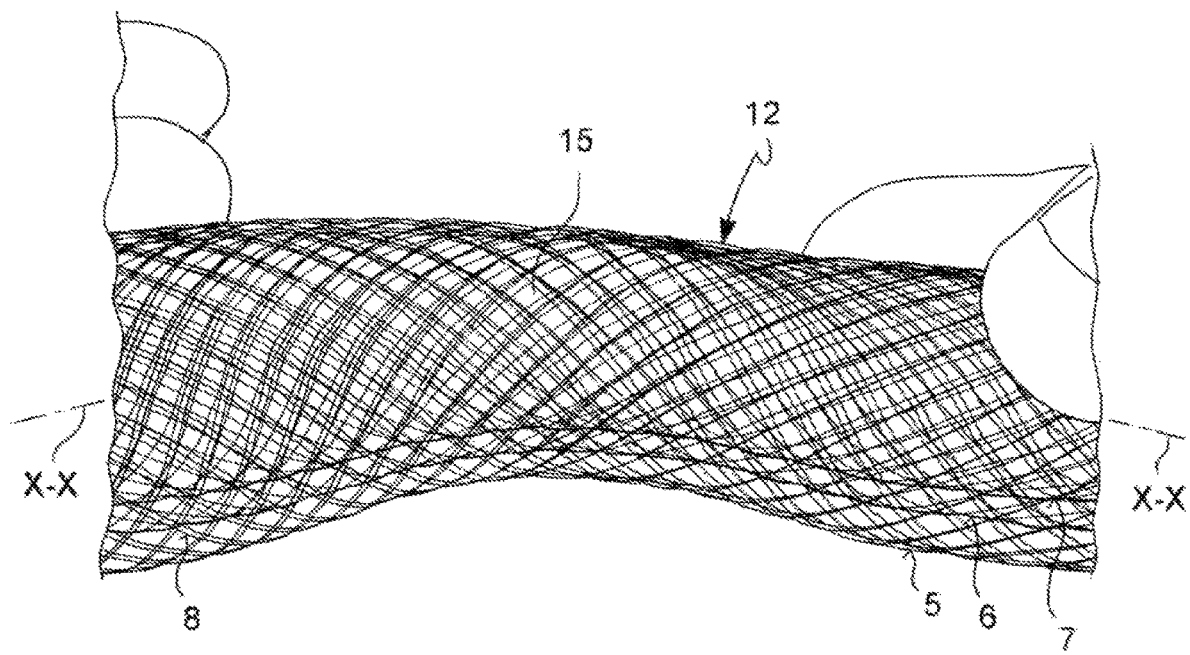
FIG. 3 shows a multilayer luminal endoprosthesis flexibly deformed by an operator.
Figure 4:
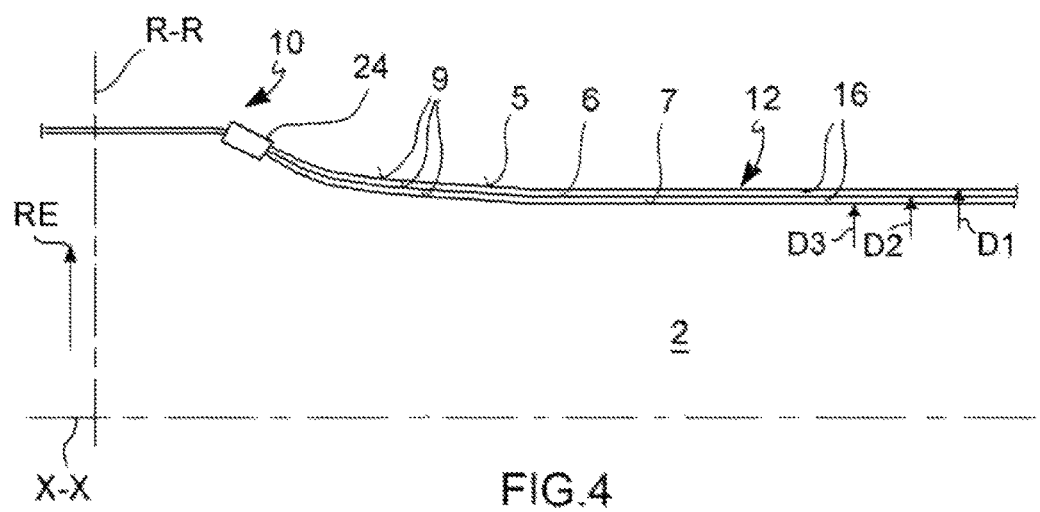
FIG. 4 shows a diagram showing a longitudinal section of a portion of a multilayer luminal endoprosthesis.
Figure 6:
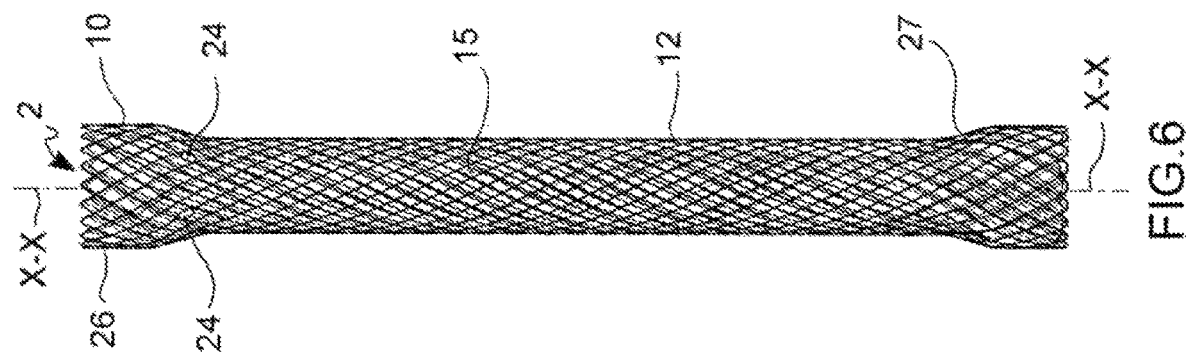
FIG. 6 shows a vertical elevation view of a luminal endoprosthesis, according to one embodiment.
Figure 5:
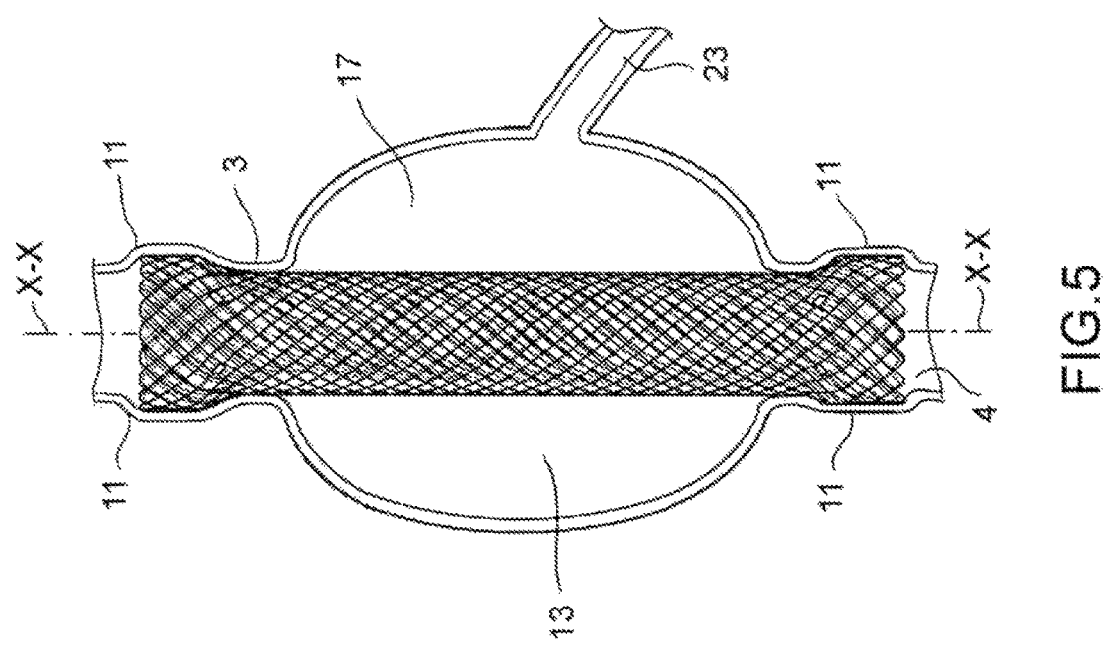
FIG. 5 shows a luminal endoprosthesis implanted in an implantation site comprising a pathological portion.
Figure 7:
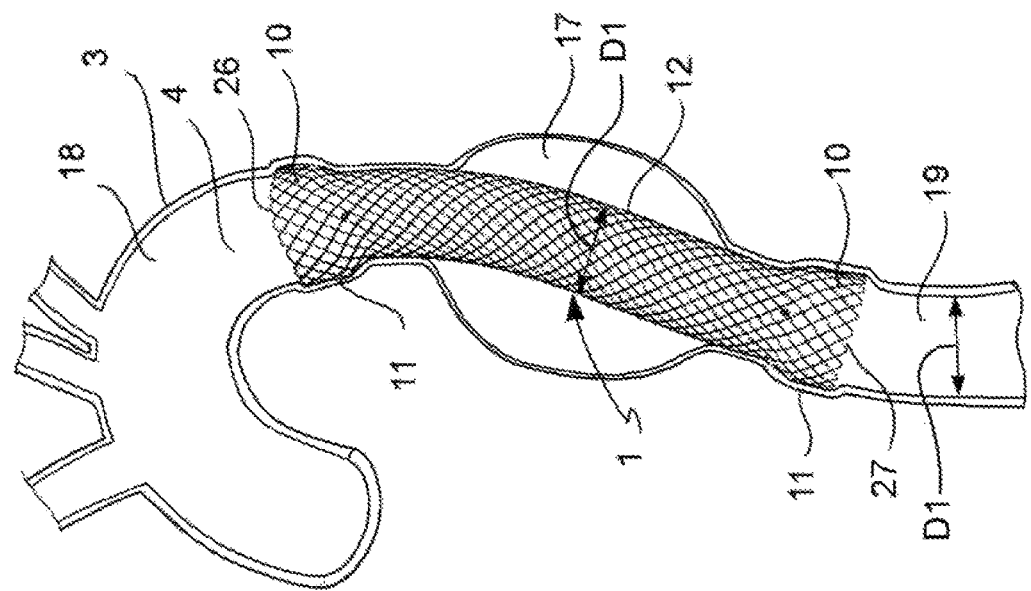
Figure 8:
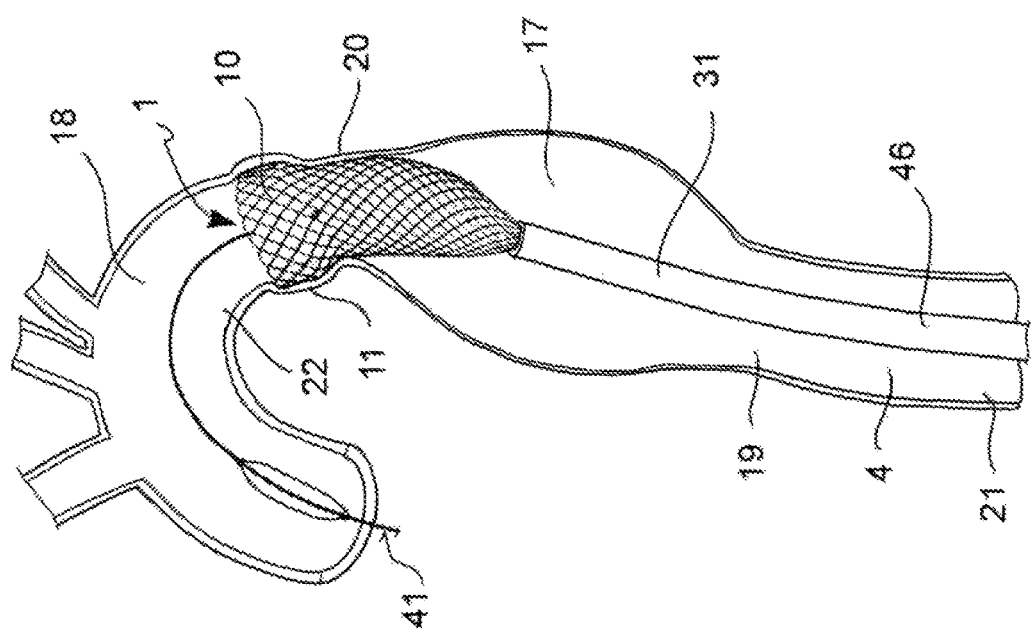
Figure 9:
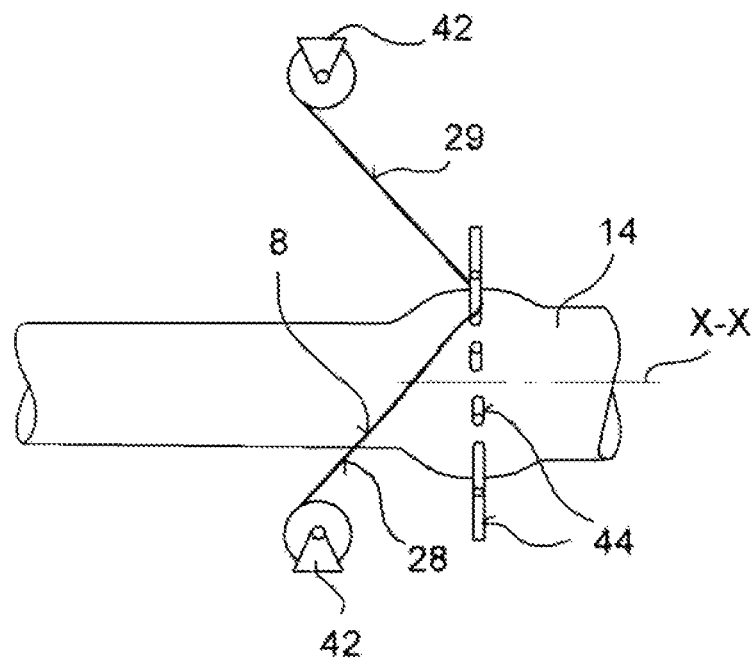
Figure 10:
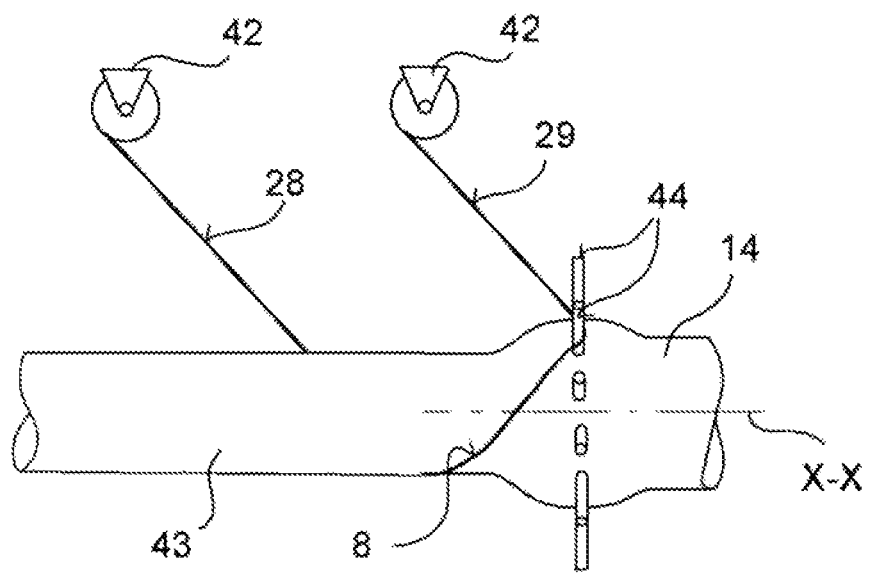
Figure 11:
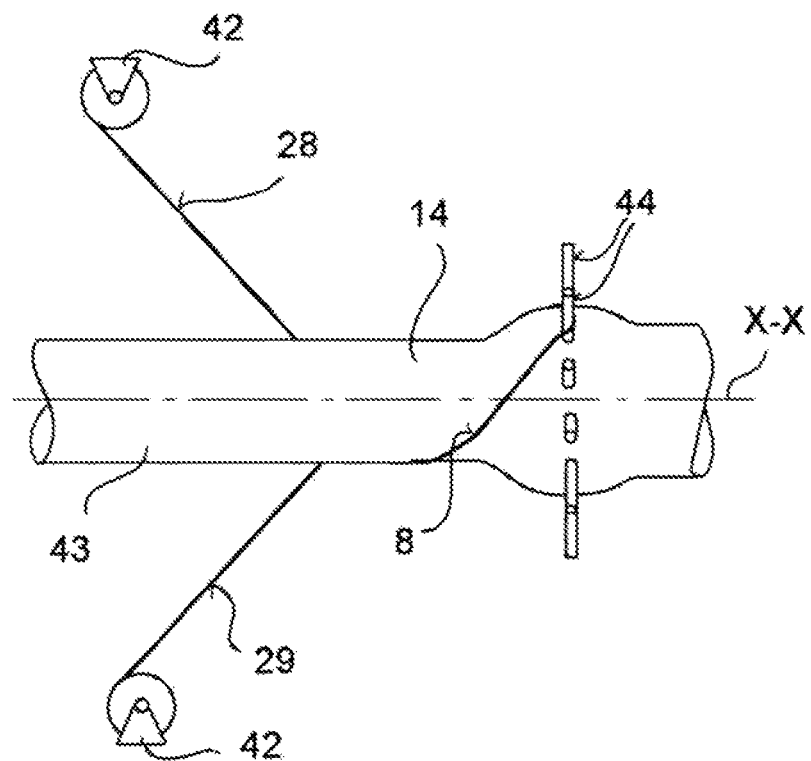
Figure 12:
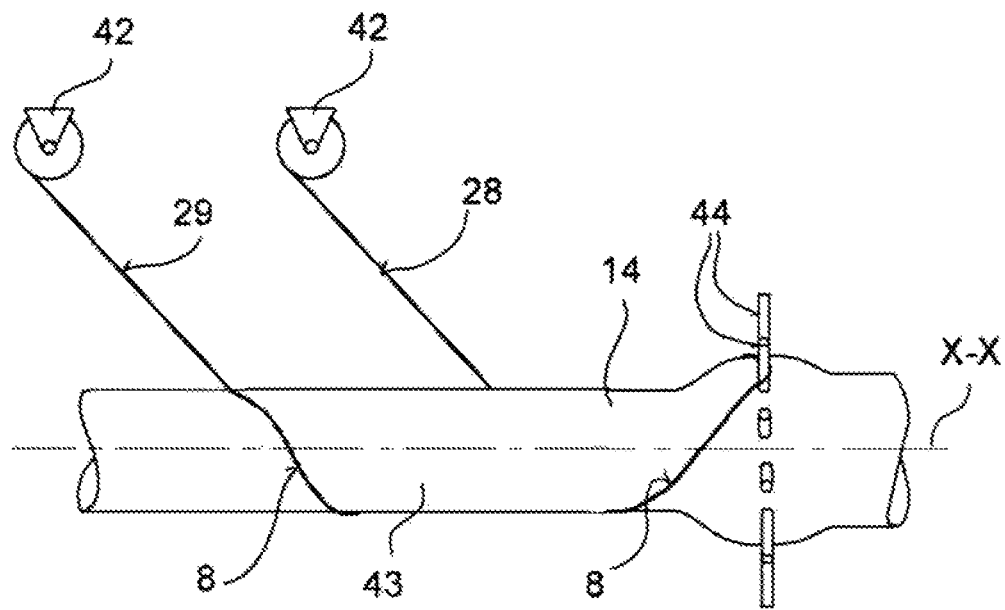
Figure 13:
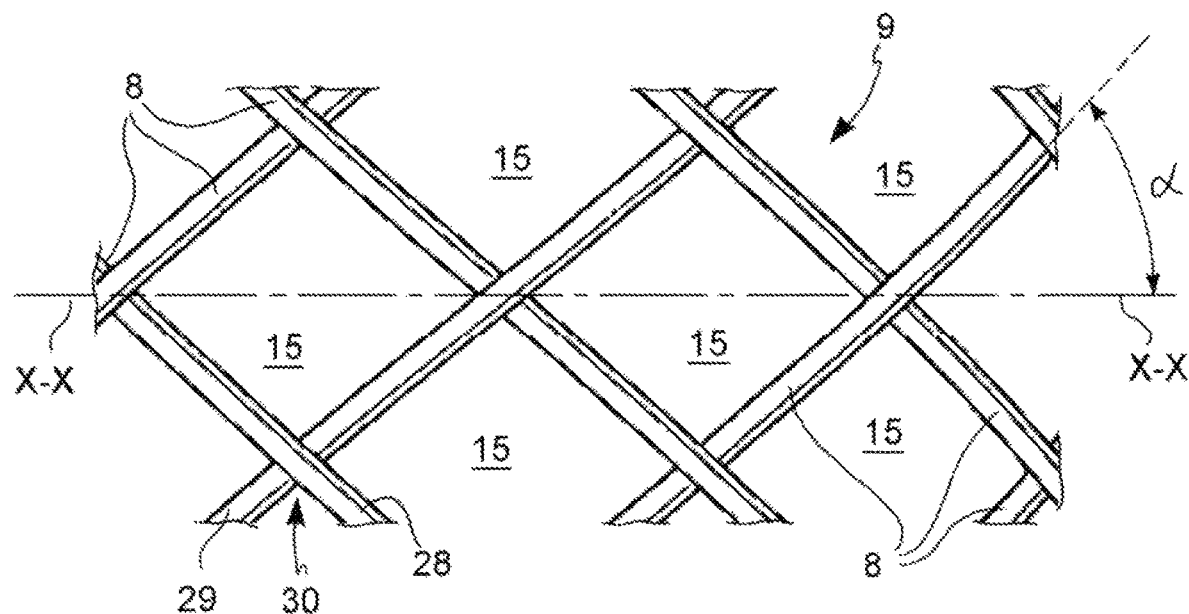
Figure 14:
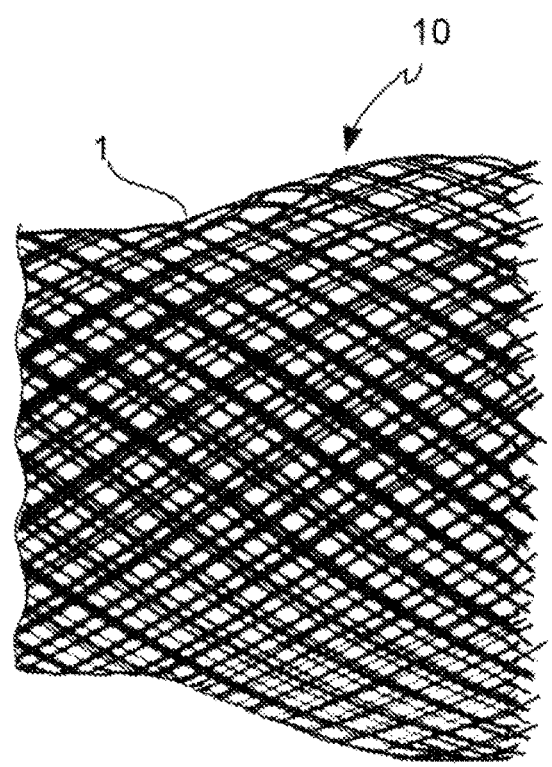
Figure 15:
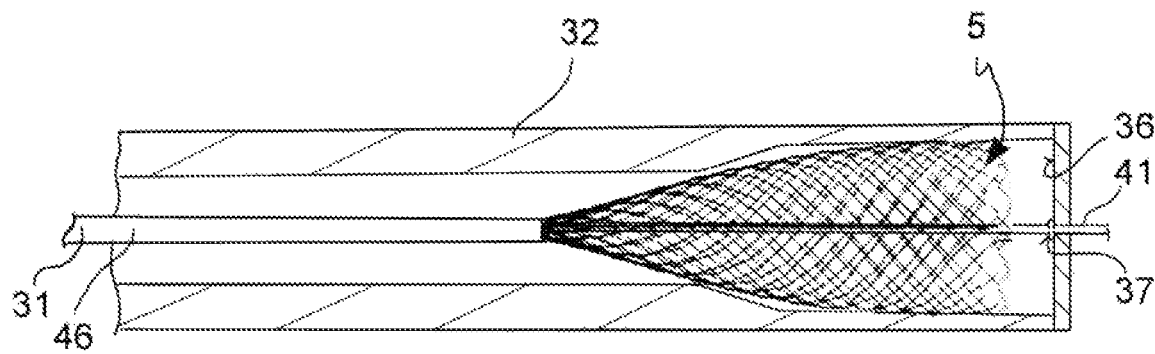
Figure 16:
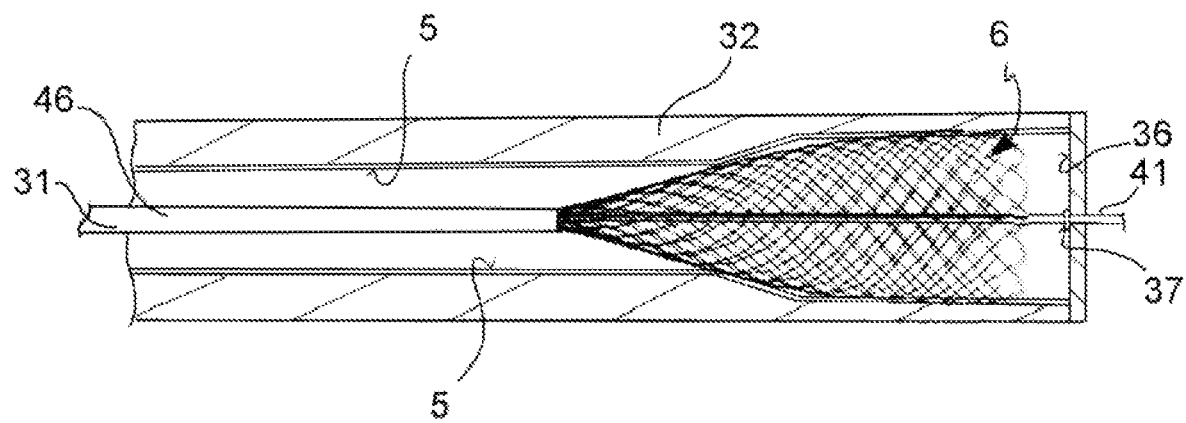
Figure 17:
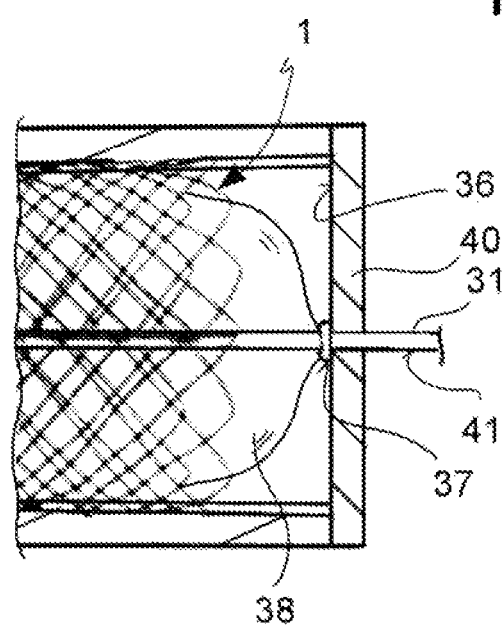
Figure 18:
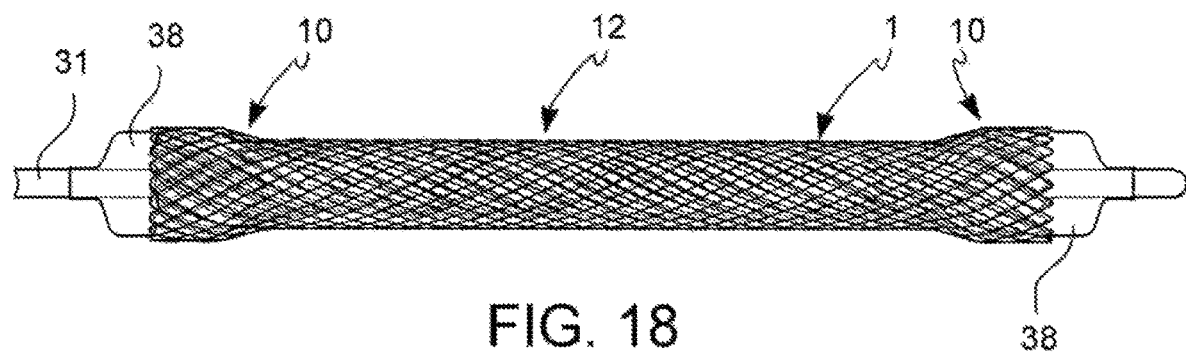
Figure 19:
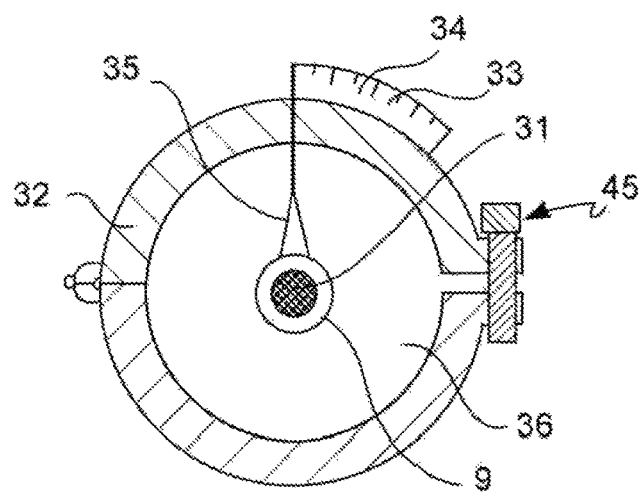
Figure 20:
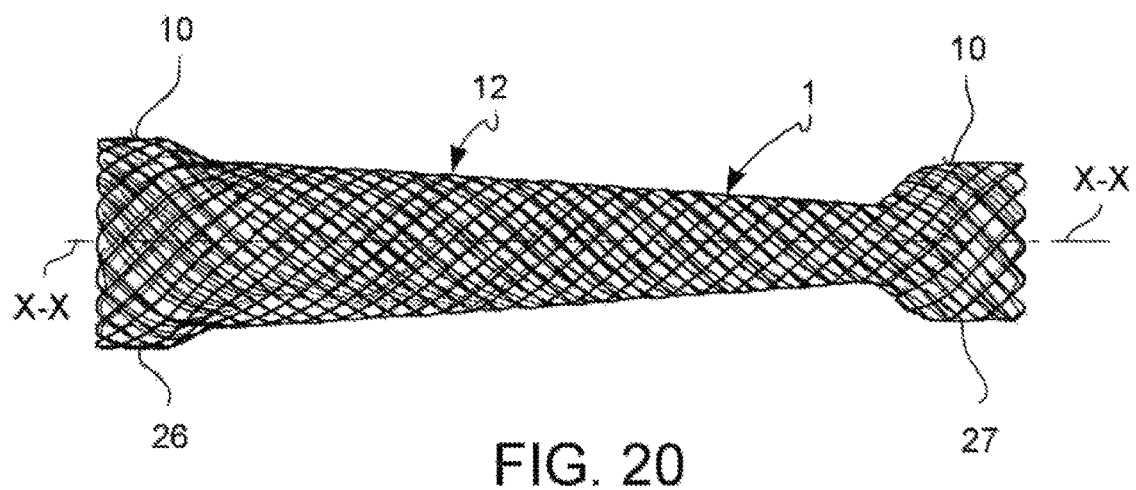
Figure 23:
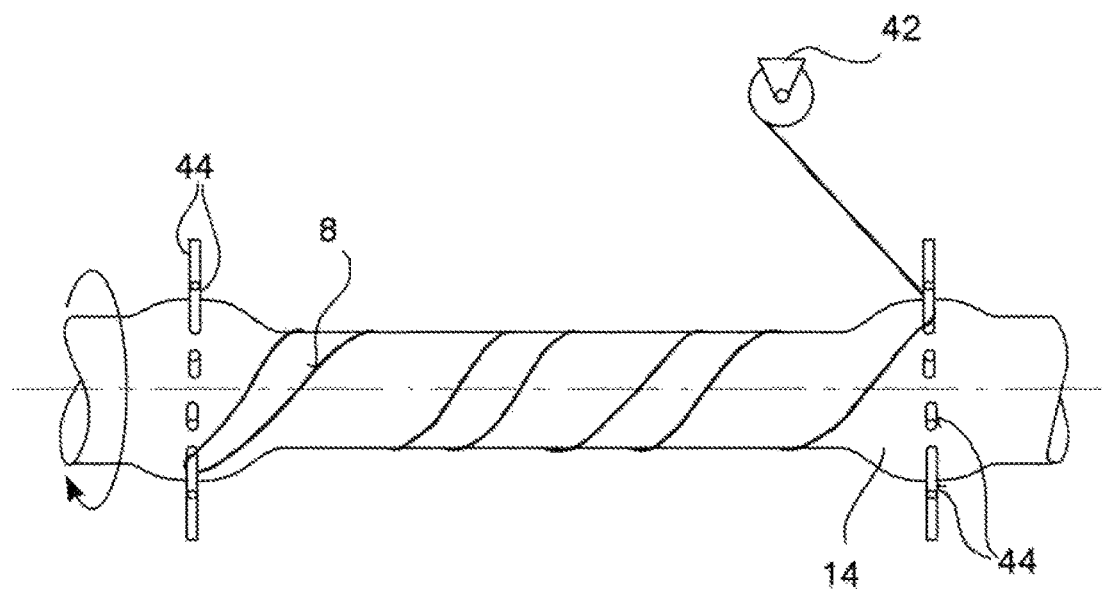
Figure 24:
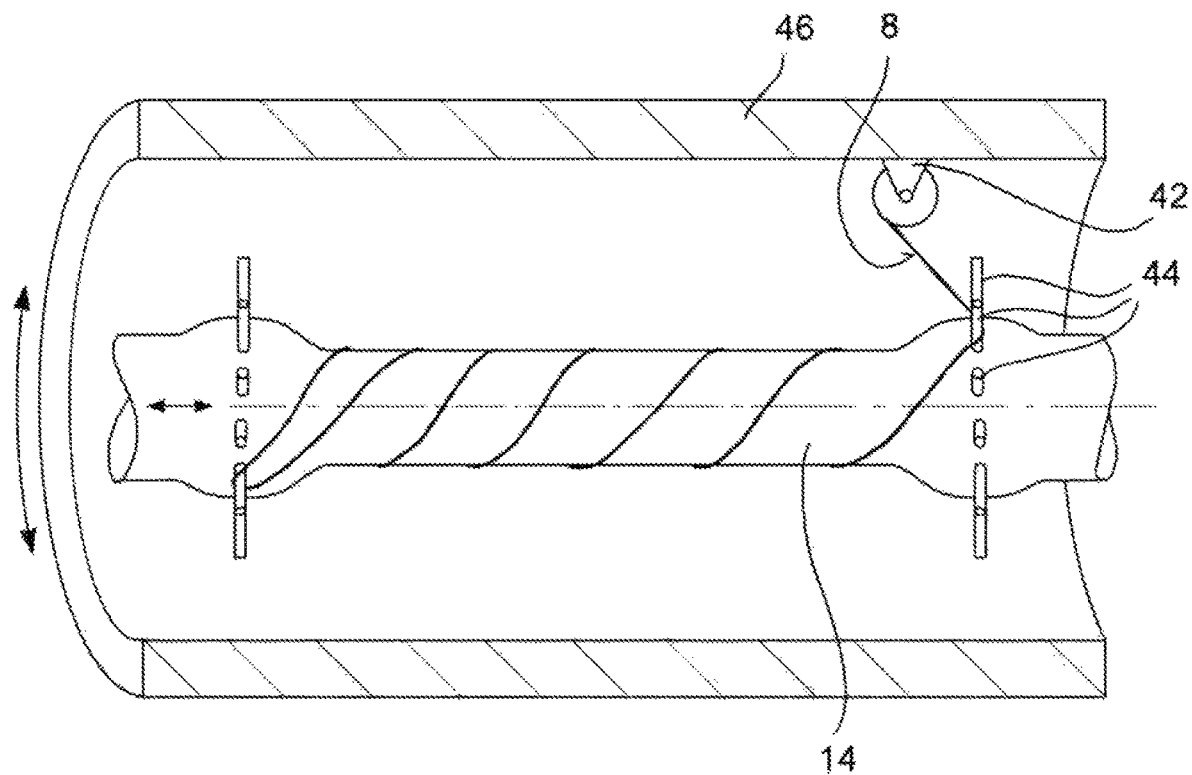
Figure 25:
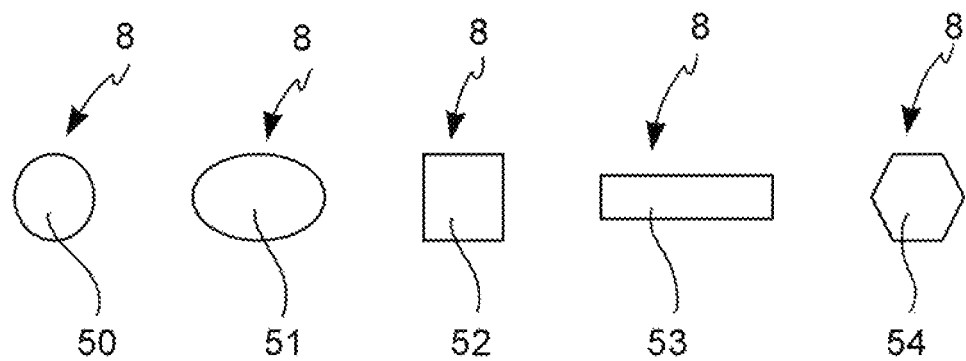
Figure 26:
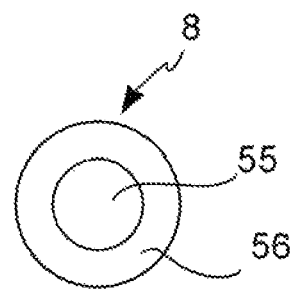
Figure 27:
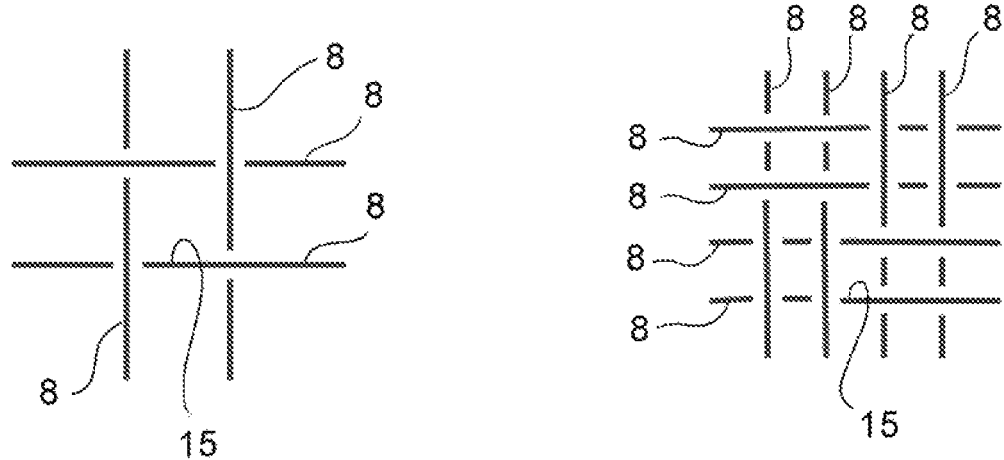
Figure 28:
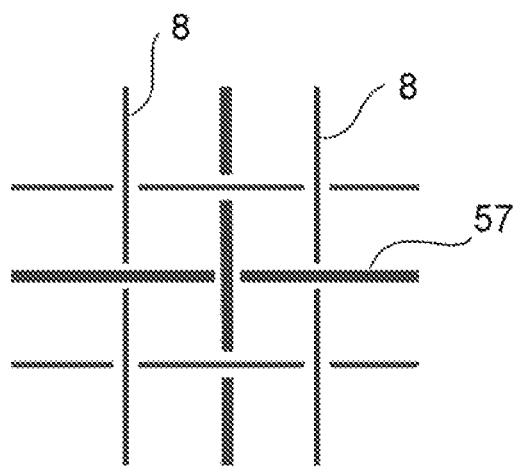
Figure 29:
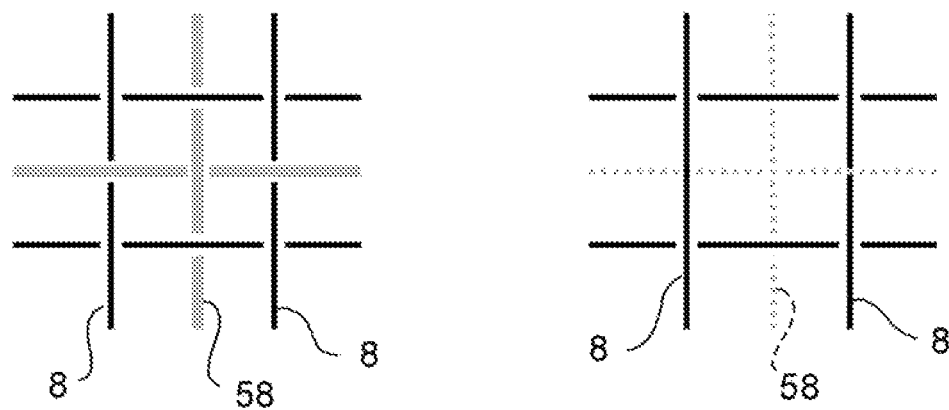
Figure 30:
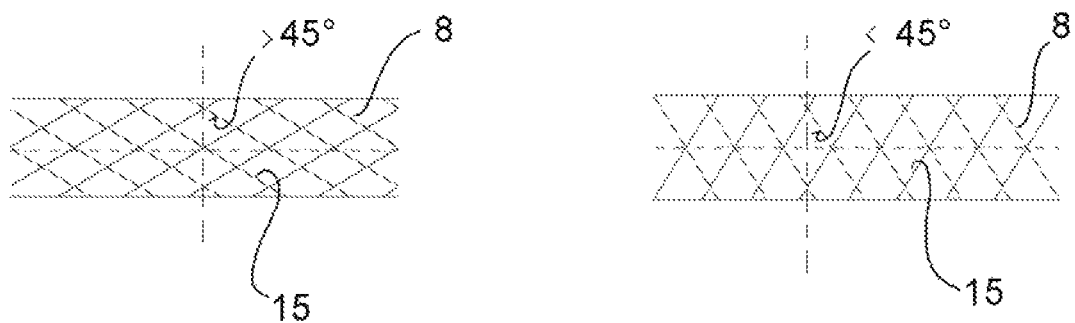
Figure 31:
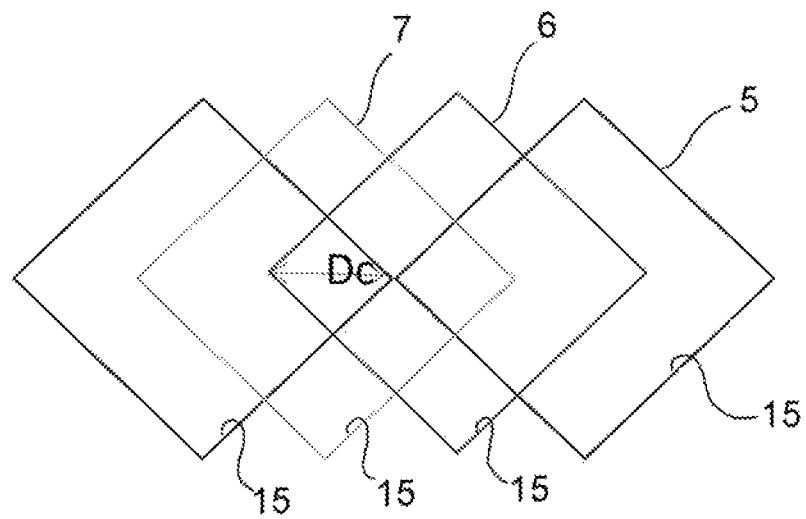
Figure 32:
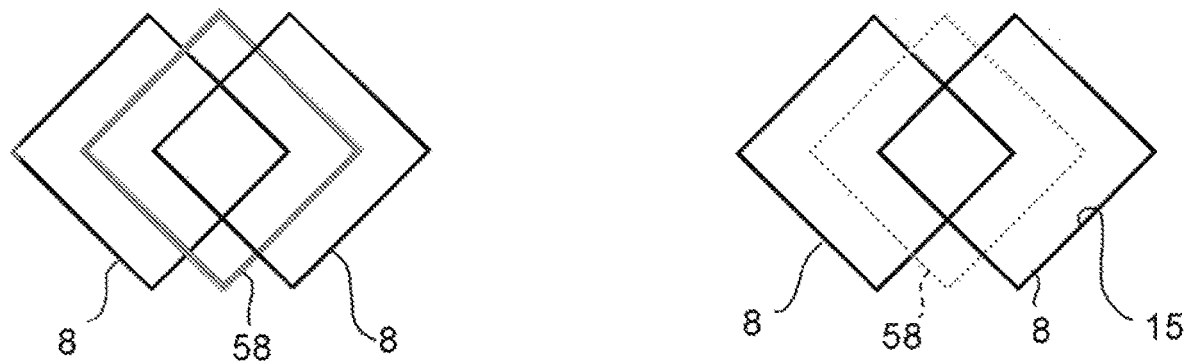
Figure 33:
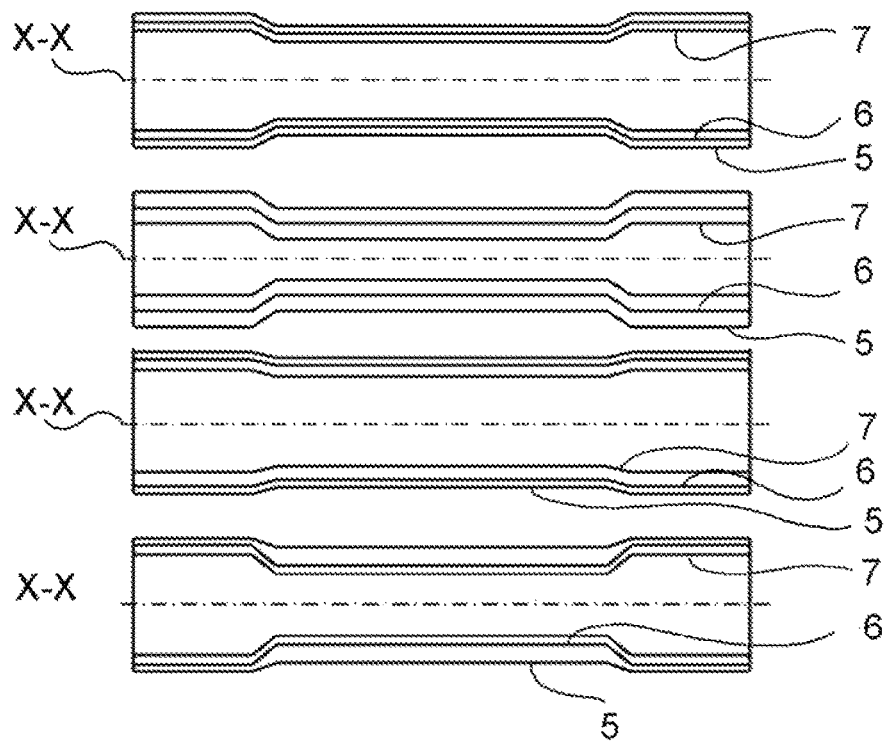
Figure 34:
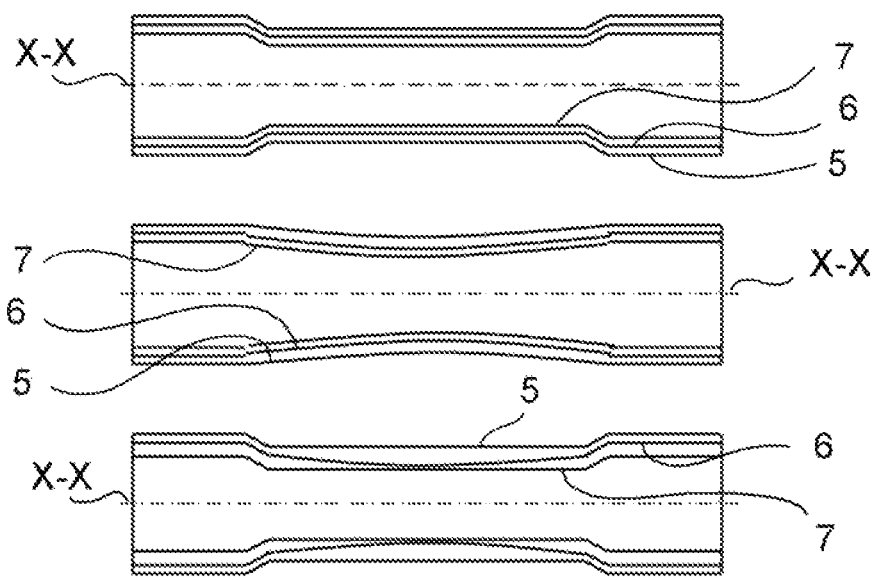
Figure 35:
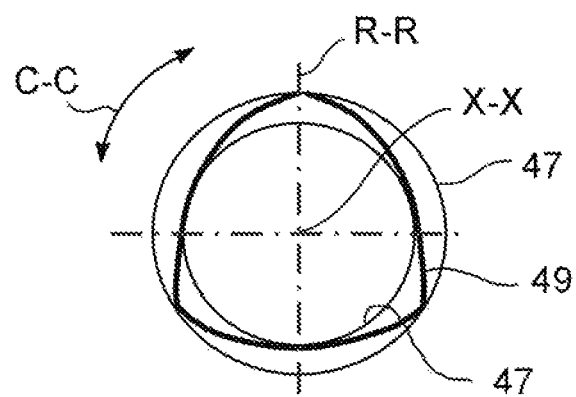
Figure 36:
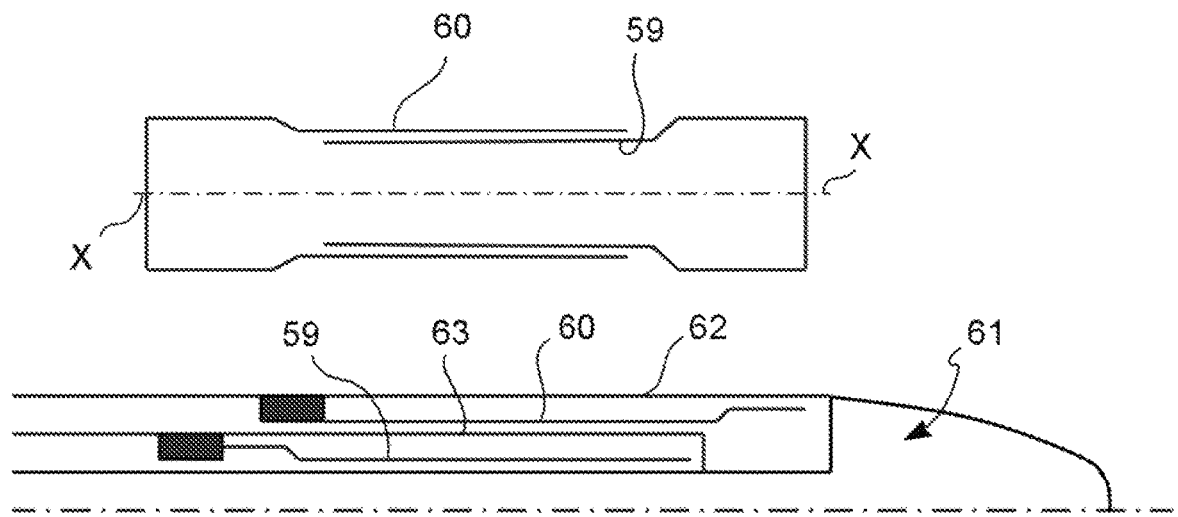
Figure 37:
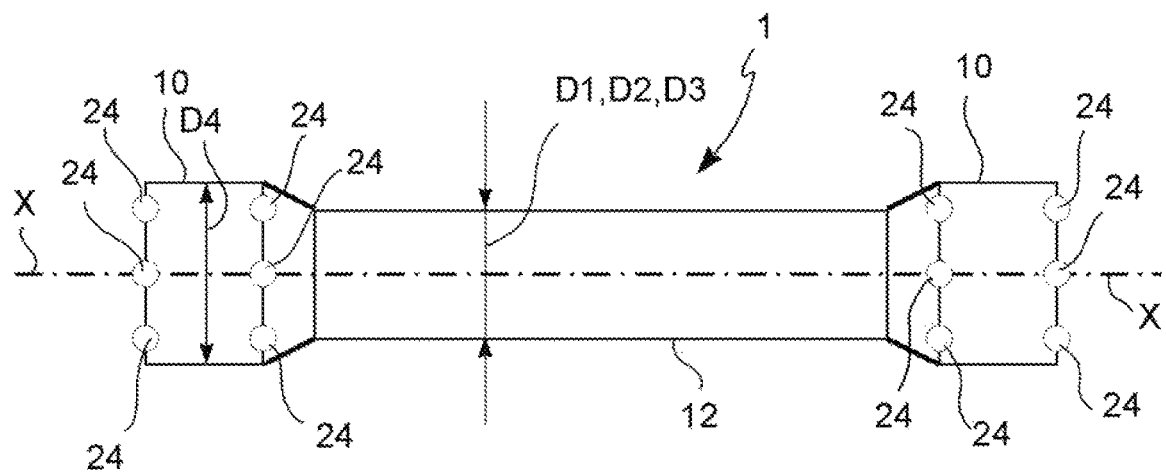
Figure 38:
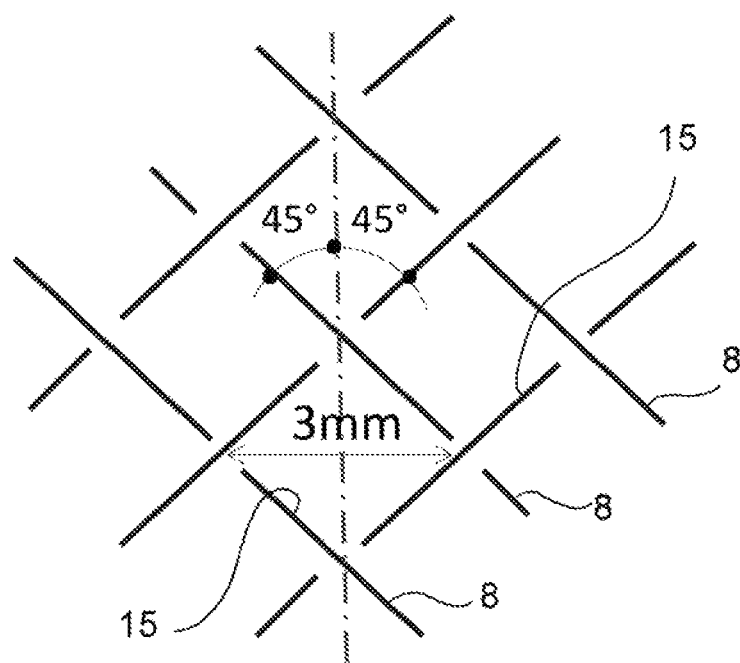
Figure 39:
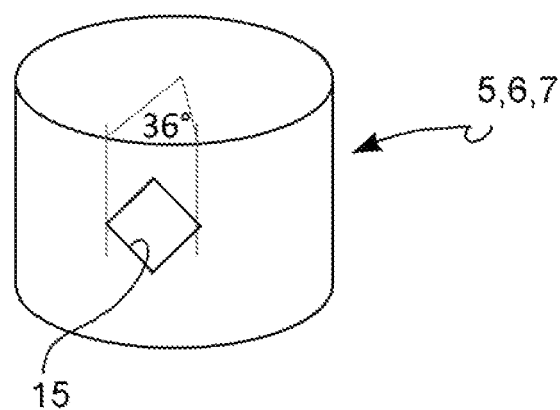
Figure 40:
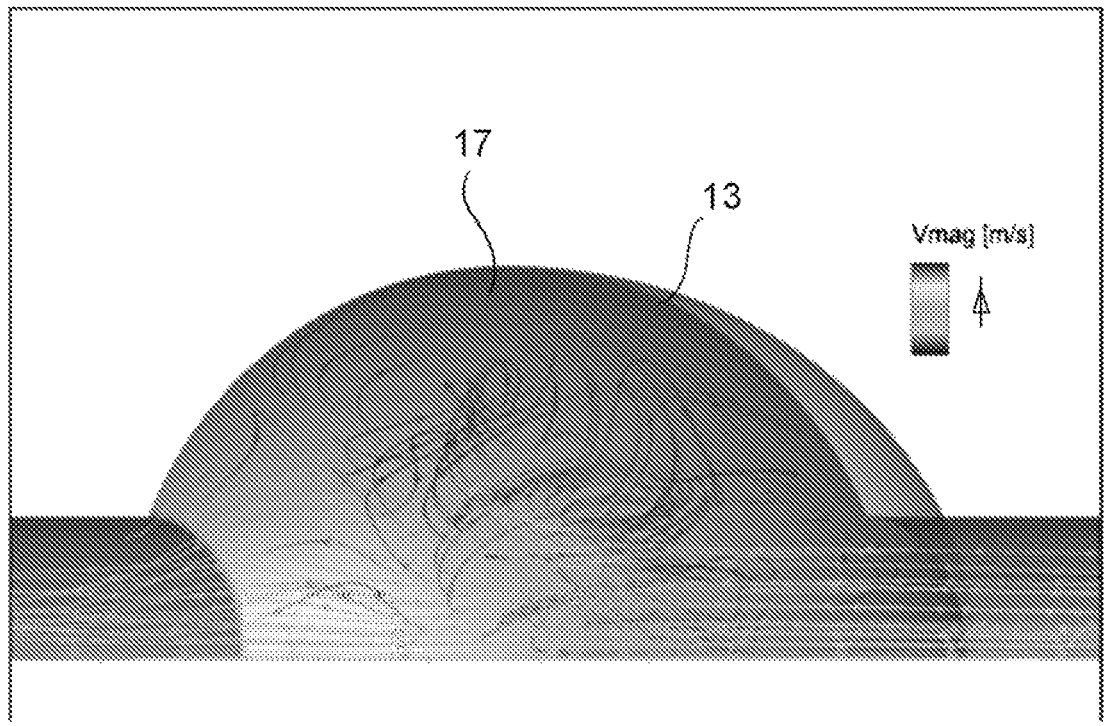
Figure 41:
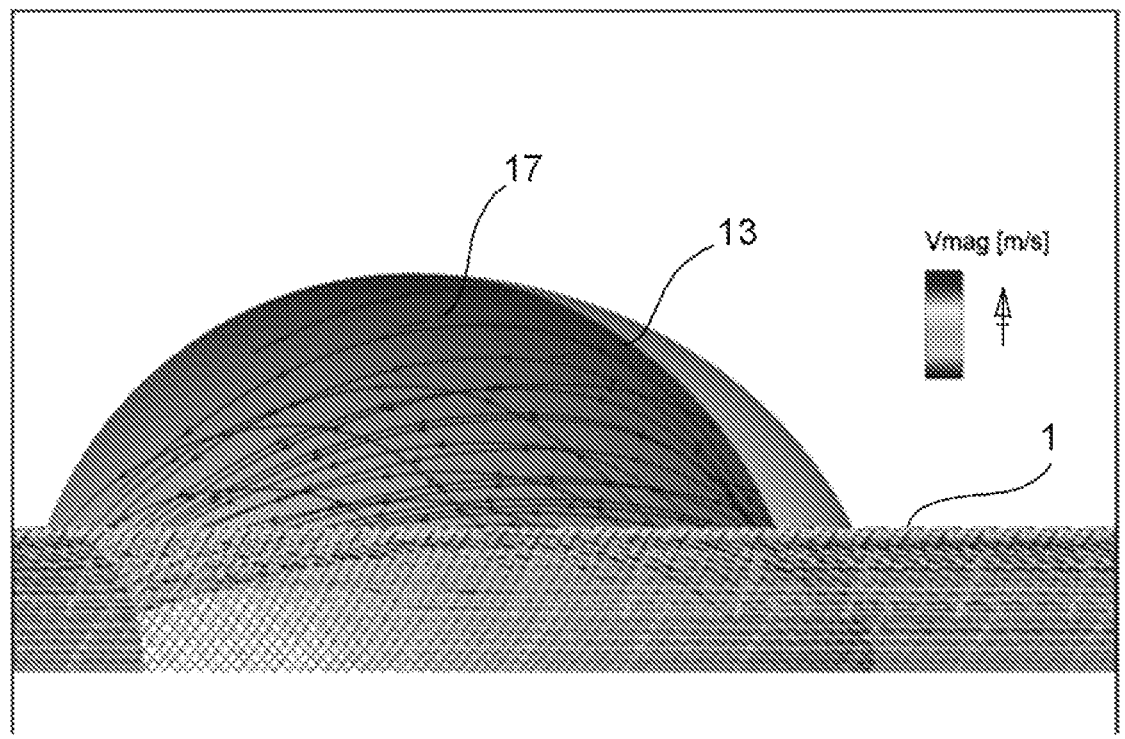

FIGS. 7 and 8 schematically show some possible steps of a process of delivery and delivery of a luminary endoprosthesis in an implantation site comprising a pathological portion;

FIGS. 9, 10, 11 and 12 schematically show some possible steps of a manufacturing method of a luminal endoprosthesis, according to a possible mode of operation;

FIG. 13 shows a portion of an armor of a layer of a multilayer luminal endoprosthesis, according to one embodiment;

FIG. 14 shows a portion of a luminal endoprosthesis, according to one embodiment;

FIGS. 15, 16, 17 and 18 show some possible steps of a manufacturing method of a luminal endoprosthesis, according to a possible mode of operation;

FIG. 19 shows a cross-section of a support device which receives a release device which mounts an armor of a layer of a luminal endoprosthesis in a radially contracted form;

FIG. 20 shows a vertical elevation view of a luminal endoprosthesis, according to one embodiment;

FIG. 21 shows an isometric view with partially sectional parts for clarity, a possible step of a manufacturing method of a luminal endoprosthesis, according to a possible mode of operation;

FIG. 22 schematically shows a connecting element of a luminal endoprosthesis, according to one embodiment;

FIG. 23 schematically shows a possible step of a manufacturing method of a luminal endoprosthesis, according to a possible mode of operation;

FIG. 24 schematically shows, with partially sectional parts for clarity, a possible step of a manufacturing method of a luminal endoprosthesis, according to a possible mode of operation;

FIG. 25 shows five examples of cross-section of the threadlike element with which the armor of the layer of the luminal endoprosthesis assembly is made;

FIG. 26 shows a further cross-section of a threadlike element comprising a core of a first material covered by a second material;

FIG. 27 shows two details of armors made with a threadlike element which forms said armors with its interlacing, according to two embodiments of said interlacing;

FIG. 28 shows a detail of the armor made with two threadlike elements which form said armor with their interlacing, according to an embodiment of said interlacing;

FIG. 29 shows a detail of the armor made with two threadlike elements which form said armor with their interlacing, according to an embodiment of said interlacing and at two different time points of the assembly;

FIG. 30 shows a longitudinal portion of a layer of the assembly in which the detail of armors made with a threadlike element is shown, forming said armors with its interlacing at mutually different winding angles;

FIG. 31 shows windows of three superimposed layers which form the overall porosity of the luminal endoprosthesis assembly;

FIG. 32 shows windows of three superimposed layers which form the overall porosity of the luminal endoprosthesis assembly consisting of two threadlike elements and at two different time points of the assembly;

FIG. 33 shows a schematic view of four different longitudinal sections of luminal endoprosthesis assemblies made with three layers of different transversal dimensions which create different clearances or cavities between one layer and the adjacent layer;

FIG. 34 schematically shows three further and different longitudinal sections of luminal endoprosthesis assemblies made with three layers of different transversal dimensions which create different clearances or cavities between one layer and the adjacent layer;

FIG. 35 schematically shows a cross-sectional view of the longitudinal axis of a luminal endoprosthesis assembly made of three layers of different cross-sections which create clearances or cavities between one layer and the adjacent layer;

FIG. 36 schematically shows a luminal endoprosthesis assembly made of layers having two mutually telescoping components and a stent delivery system for delivering said assembly in a vessel and releasing said assembly by regulating with a sequential opening of the sheaths the desired length of the telescopic assembly;

FIG. 37 shows a longitudinal section view of a luminal endoprosthesis assembly made with layers having identical geometry;

FIG. 38 shows a detail of the armor made with a threadlike element which forms said armor with its interlacing, according to one embodiment;

FIG. 39 schematically shows an isometric view of a longitudinal stretch of a layer of said assembly in which the angle at the center of development of a window of the interlacing forming said armor is shown;

FIGS. 40 and 41 show a flow test of a blood vessel having an aneurysmal pathology in which initially the luminal endoprosthesis assembly in FIG. 40 is not present and the endoprosthesis assembly in FIG. 41 is present, highlighting a strong reduction and regularization of the flow.

DESCRIPTION OF SOME PREFERRED EMBODIMENT EXAMPLES

According to a general embodiment, a luminal endoprosthesis 1 is provided.

According to a preferred embodiment, said luminal endoprosthesis 1 comprises a stent.

According to a preferred embodiment, said luminal endoprosthesis is a stent.

Said luminal endoprosthesis 1 delimits at least partially a prosthesis lumen 2 and is suitable for the implant in an anatomical structure 3 which at least partially defines at least one cavity 4. According to an embodiment, said anatomical structure 3 is a blood vessel, for example an artery, for example the aorta, said cavity 4 is a vascular lumen of said blood vessel and said luminal endoprosthesis 1 is a vascular luminal endoprosthesis suitable for endovascular implantation. According to an embodiment, said luminal endoprosthesis 1 has a substantially tubular shape.

Said luminal endoprosthesis 1 is particularly suitable, but not univocally intended, for the treatment of an aneurysm 17. According to an embodiment, said luminal endoprosthesis 1 is particularly suitable, but not univocally intended, for the treatment of aneurysms of the aortic arch 18, or of the descending aorta 19, for example of the thoracic aorta 20, of the abdominal aorta 21 or of the aortic isthmus 22.

According to an embodiment variant, said anatomic structure 3 is an esophagus and said cavity 4 is the lumen of the esophagus.

In said luminal endoprosthesis 1 a longitudinal direction X-X is defined, substantially parallel to or coinciding with the longitudinal axis of development of said luminal endoprosthesis 1, a radial direction R-R, orthogonal to the longitudinal direction X-X, and a circumferential or tangential direction, orthogonal to both the longitudinal direction X-X and to the radial direction R-R. An external radial direction RE is also defined, directed along the radial direction away from the longitudinal axis of development of the luminal endoprosthesis 1 and an internal radial direction, opposite to said external radial direction RE.

Said luminal endoprosthesis 1 is a multilayer luminal endoprosthesis and comprises two or more layers 5, 6, 7.

According to a preferred embodiment, said two or more layers are exactly three layers 5, 6, 7.

According to a preferred embodiment, said luminal endoprosthesis 1 comprises three armors 9 which form said three layers 5, 6, 7.

The layers, for example but not necessarily the three layers of which the endoprosthesis or device is made, according to an embodiment, are separated from each other, for example in the portion thereof facing the pathological region, for example in rest conditions or nominal conditions they have a space or a predefined distance between them, i.e. between each layer, for example variable between 0.1 mm and 3 mm, to allow the continuous oscillation thereof and the reciprocal sliding, as occurs in the tunica media of a normal subject. Said space is a space with no interruption at least along the entire working portion 12 of the endoprosthesis. According to an embodiment, the distance between the layers is defined in such a way that the endothelial cells never adhere between the layers, preventing them from forming a bridge-like connection between the layers, to prevent a compaction thereof and thus avoiding that the flow in the collateral vessels that branch off the aorta is prevented, always ensuring the patency of these collateral vessels.

According to a preferred embodiment, said two or more layers comprise a first layer 5 having a predetermined nominal caliber of first layer D1, a second layer 6 having a predetermined nominal caliber of second layer D2 smaller than said nominal caliber of first layer D1, and a third layer 7, having a predetermined nominal caliber of third layer D3 smaller than both said nominal caliber of first layer (D1) and said nominal caliber of second layer D2. According to an embodiment, said two or more layers are coaxial.

At least one layer 5 or 6 or 7 of said two or more layers 5, 6, 7 comprises at least one threadlike element 8, 38, 48 forming an armor 9. According to an embodiment, each layer 5 or 6 or 7 of said two or more layers 5, 6, 7 comprises said at least one threadlike element 8.

According to an embodiment, said first layer 5 comprises a first threadlike element 8, said second layer 6 comprises a second threadlike element 38 and said third layer comprises a third threadlike element 48.

According to a preferred embodiment, at least one layer 5 or 6 or 7 of said two or more layers 5, 6, 7 comprises a single threadlike element 8, 38, 48 forming an armor 9. In this way, it is possible to make a layer with a single threadlike element 8, 38, 48. According to an embodiment, each layer 5 or 6 or 7 of said two or more layers 5, 6, 7 comprises a single threadlike element 8, 38, 48.

According to a preferred embodiment, said armor 9 is an interlaced armor which forms a lattice.

According to an embodiment, said at least one threadlike element 8, 38, 48 develops in a substantially helical manner in said armor 9.

According to an embodiment, said armor 9 is an interlaced armor which forms a fabric, according to an embodiment, a fabric of the weft and warp type, or of the open-mesh type, in which two opposite ends 28, 29 of said at least one threadlike element 8, 38, 48 are alternately crossed at crossing sites 30. According to an embodiment, some crossing sites 30 have a first threadlike element end 28 arranged radially outwardly to a second threadlike element end 29 and some crossing sites 30 have a second threadlike element end 29 arranged radially outwardly to a first threadlike element end 28.

According to an embodiment, said first threadlike element end 28 and said second threadlike element end 29 form a crossing angle α with respect to the longitudinal axis of the luminal endoprosthesis 1. According to an embodiment, said crossing angle α is between 30° and 60°. According to an embodiment, said crossing angle α is between 40° and 50°, and according to an embodiment, said crossing angle α is substantially equal to 45°. Due to the provision of said crossing angle α, it is possible to mimic the alignment of the endothelial cells of the wall of a native blood vessel, for example of a portion of the native aorta. In fact, as is known, endothelial cells of a wall of a native blood vessel are aligned with the mean blood stream direction during the systolic phase, and the blood stream during the systolic phase can proceed substantially helix- or spiral-wise.

According to an embodiment, said two opposite ends 28, 29 of a single threadlike element 8, 38, 48 are connected to each other by means of an end connecting device 25. According to an embodiment, the end connecting device 25 is suitable for forming a rigid connection between said two opposite ends 28, 29.

Said luminal endoprosthesis 1 comprises at least one anchoring portion 10, suitable for anchoring to an anatomical portion 11 of the walls of the cavity 4 of the anatomical structure 3. Said anchoring portion 10 is suitable for forming a substrate which favors the adhesion of the newly formed vascular endothelial tissue, similar to a scaffold.

Said luminal endoprosthesis 1 comprises at least one working portion 12, suitable for facing a pathological portion 13 of the anatomical structure 3. For example, said pathological portion 13 is an aneurysmal sac.

Due to the provision of at least one anchoring portion 10 and at least one working portion 12, said luminal endoprosthesis 1 is capable of anchoring to a substantially healthy portion of the anatomical structure 13. Due to the provision of at least one anchoring portion 10 and at least one working portion 12, said luminal endoprosthesis 1 protrudes along said pathological portion said working portion 12 to reform a caliber equivalent to the healthy diameter of the vessel in which the endoprosthesis is implanted.

According to an embodiment, said anchoring portion 10 is longitudinally disjointed from said working portion 12. In other words, moving along said endoprosthesis in the longitudinal direction, said anchoring portion 10 is first encountered and then said working portion 12.

Advantageously, said two or more layers 5, 6, 7 are separated from each other, according to an embodiment radially separated, at least in said working portion 12 of the luminal endoprosthesis 1. This prevents having to provide connecting elements in said working portion 12 between one layer 5 or 6 or 7 and an adjacent layer.

According to an embodiment, said working portion 12, when not radially stressed, has a diameter or caliber D1 similar or equal to the healthy diameter D1 of the corresponding anatomical portion in which it is intended to be implanted. For example, said endoprosthesis has a working portion with a radial diameter or caliber D1 equal to the internal mean average diameter D1 of the healthy portion of aorta in which the endoprosthesis must be implanted when an aneurysm is formed in this portion of the aorta.

The provision of such a luminal endoprosthesis 1 allows to make two or more layers 5, 6, 7 which in said working portion 12 are substantially independent from each other. According to an embodiment, in the at least one anchoring portion 10, said two or more layers 5, 6, 7 are next to one another and constrained one to the at least one other.

Due to the provision of two or more layers 5, 6, 7 separated from each other in said working portion 12, it is possible to provide a space between adjacent layers 16, suitable for allowing the flow at least in the a substantially longitudinal direction X-X of a fluid, example blood, between two adjacent layers 5, 6, 7. According to an embodiment, said space between adjacent layers 16 is substantially of annular cylindrical in shape to surround delimited by two adjacent layers.

Due to the provision of two or more layers 5, 6, 7 separated from each other in said working portion 12, the relative movement is allowed between said two or more layers 5, 6, 7 even after the implant of the luminal endoprosthesis 1. In this way, the adhesion and growth of vascular endothelial cells is prevented at least on the one or more layers 6, 7 having smaller caliber D2, D3, and, according to an embodiment on all the layers 5, 6, 7 of the working portion 12 of the luminal endoprosthesis 1. For example, said two or more layers 5, 6, 7 separated from each other in said working portion 12 can move both longitudinally and circumferentially and radially with respect to one another. This imparts improved flexibility, including torsional flexibility, to the luminal endoprosthesis 1. In this way, a prolonged service life is allowed, compared to known solutions.

Due to the provision of two or more layers 5, 6, 7 separated from one another in said working portion 12, a luminal endoprosthesis 1 of improved flexibility is provided which is suitable for implantation in tortuous anatomical structures 3, such as for example the aortic isthmus 22.

According to an embodiment, such a luminal endoprosthesis 1 is suitable for embodiments having an increased longitudinal extension compared to known solutions.

According to an embodiment, said at least one threadlike element 8 is made of superelastic material. According to an embodiment, said at least one threadlike element 8 is made of material suitable for maintaining the memory of a predefined shape and reacquire it when it undergoes thermal variations and/or mechanical stresses. According to an embodiment, said at least one threadlike element 8 is at least partially made of nitinol. According to an embodiment, said at least one threadlike element 8 is at least partially made of nitinol suitable for reacquiring the predefined shape when heated and/or mechanically stressed. According to an embodiment, said at least one threadlike element 8 comprises a coating suitable for regulating the biological interaction between the luminal endoprosthesis 1 and the walls of the implant anatomical structure 3.

According to a preferred embodiment, said at least one threadlike element 8, 38, 48 of the armor 9 of each layer 5, 6, 7 defines a plurality of windows 15 suitable for putting the prosthesis lumen 2 in fluidic communication with the pathological portion 13, such as an aneurysmal sac, of the anatomical structure 3.

According to an embodiment, the armor 9 formed by the at least one threadlike element 8, 38, 48 of one layer is circumferentially or angularly offset with respect to the armor of one or more adjacent layers by a predetermined amount of offset smaller than the circumferential distance between two successive crossing sites 30 and according to an embodiment, by an amount of offset smaller than one third of the circumferential distance between two successive crossing sites 30. In this way, said plurality of windows 15 of one layer is substantially offset with the plurality of windows 15 of one or more adjacent layers but at the same time, the windows 15 of adjacent layers are substantially aligned so that said luminal endoprosthesis 1 is suitable for putting said prosthesis lumen 2 in fluidic communication with the pathological portion 13 of the anatomical structure 3. According to an embodiment, the alignment between the windows 15 of adjacent layers is selected in such a way as to filter the elements of greater size, for example thrombi, to prevent them from moving, by convection or diffusion, from the prosthesis lumen towards the pathological portion 13, for example the aneurysmal sac.

According to an embodiment, said space between adjacent layers 16 is in fluidic communication with said prosthesis lumen 2 through the plurality of windows 15 of the layers 6, 7 radially internal to said space between adjacent layers 16. In this way, the flow of fluid, for example blood, is allowed to flow from the prosthesis lumen 2 to the pathological portion 13, for example an aneurysmal sac, and vice versa from the pathological portion 13, for example an aneurysmal sac, towards the prosthesis lumen 2.

Due to the provision of two or more layers 5, 6, 7 separated from each other in said working portion 12, it is possible to mimic or reproduce the behavior of the structure of the tunica media of a native blood vessel.

Due to the provision of such a luminal endoprosthesis 1, it is possible to generate a flow diversion that strongly reduces the turbulence of the blood stream in the aneurysmal sac, allowing the pressure on the walls of the aneurysmal sac to be reduced, thus preventing the rupture of the walls of the aneurysmal sac and thus favoring the reabsorption of the aneurysm. The provision of said plurality of windows 15 allows to make the blood stream into the aneurysmal sac substantially laminar and at the same time allows to maintain the patency of the aneurysmal sac as well as the collateral vessels 23 distally branching off it, where present. In this way, it is possible to still feed the biological tissues facing the aneurysmal sac, albeit in a weakened manner.

According to an embodiment, said at least one anchoring portion 10 comprises at least one layer connecting device 24 between said two or more layers 5, 6, 7. According to an embodiment, said layer connecting device 24 between said two or more layers 5, 6, 7 forms a rigid connection, thus being not suitable for allowing the relative movement between adjacent layers in said anchoring portion 10. According to an embodiment, said layer connecting device 24 and said end connecting device 25 are the same connecting element 24, 25, for example a metal element, for example a sleeve for pressure or crimping connection. According to an embodiment, at least one of said layer connecting device 24 and said end connecting device 25 is made of radio-opaque material, so as to make the luminal endoprosthesis 1 detectable by bioimaging acquisition equipment, for example radiological equipment, after implantation in the anatomical structure 3.

According to an embodiment, said at least one anchoring portion 10 of said luminal endoprosthesis comprises at least two, and according to an embodiment at least three, connecting elements 24, 25 equally spaced in a circumferential direction and placed substantially at the same height along the longitudinal direction X-X.

According to a preferred embodiment, said luminal endoprosthesis comprises at least two anchoring portions 10 longitudinally opposite with respect to said at least one working portion 12. According to an embodiment, said at least two opposite anchoring portions 10 are located at opposite ends 26, 27 of said luminal endoprosthesis 1. Said opposite ends 26, 27 comprise a proximal end 26 and a distal end 27. According to a preferred embodiment, said at least one anchoring portion 10 has a smaller longitudinal extension with respect to said working portion 12.

According to a preferred embodiment, said at least one anchoring portion 10 has a larger caliber with respect to said at least one working portion 12. According to a preferred embodiment, all the layers 5, 6, 7 of said at least one anchoring portion 10 have a larger caliber with respect to said at least one working portion 12.

The provision of said anchoring portion 10 allows a radial thrust to act on the walls of the anatomical portion 11 which maintains the luminal endoprosthesis 1 in position in the anatomical structure 3 in which it is implanted. According to an embodiment, said at least one anchoring portion 10 is of size and material suitable for exerting a radial preload on the walls of the anatomical portion 11.

According to a preferred embodiment, said luminal endoprosthesis 1 has a shape substantially as a dog bone, comprising opposite ends 26, 27 larger than the portion of the luminal endoprosthesis 1 longitudinally interposed between said two opposite ends 26, 27.

According to an embodiment, said working portion 12 has a substantially frustoconical shape. In this way, said luminal endoprosthesis 1 is suitable for mimicking the shape of the wall of a blood vessel, for example an artery, having a caliber that is distally reduced. According to an embodiment, said distal end 27 has smaller caliber than said proximal end 26.

According to an embodiment, said anchoring portion 10 has a substantially frustoconical shape having taper which increases towards an end of the endoprosthesis 1.

According to an embodiment, said at least one threadlike element 8, 38, 48 is a thread.

According to an embodiment, said at least one threadlike element 8, 38, 48 is substantially in the form of a tape or strip having a transversal dimension that is significantly larger than its thickness.

According to an embodiment, said luminal endoprosthesis 1 is a stent-no-graft. In other words, it is a luminal endoprosthesis without textile fibers.

According to an embodiment variant, at least one layer of said two or more layers 5, 6, 7 comprises a graft fabric to form at least a portion of said luminal endoprosthesis 1. According to an embodiment, said graft fabric is associated with the armor 9 of a layer. According to an embodiment, said graft fabric is associated with said anchoring portion 10 by at least one connecting element 24, 25.

According to an embodiment, said luminal endoprosthesis 1 comprises a bifurcation of the prosthesis lumen 2, so as to be suitable for implants in anatomical structures 3 comprising a pathological portion 13 which are provided with bifurcations, such as for example the bifurcation of the iliac arteries distal to the descending stretch of the aorta.

According to a preferred embodiment, said luminal endoprosthesis is self-expanding. Said luminal endoprosthesis 1 is suitable for being delivered and released into a predefined implantation site within said anatomical structure 3 by a release device 31, for example a catheter, on which it is mounted in a radially contracted configuration. For example, said release device 31 comprises a guiding element 41 and a loading cannula 46 suitable for receiving said luminal endoprosthesis 1, as well as the armor 9 of at least one layer of said luminal endoprosthesis 1.

A method of manufacturing a multilayer luminal endoprosthesis according to any one of the previously described embodiments will be described below.

A method of manufacturing a multilayer luminal endoprosthesis 1 comprises at least the following steps.

A. Arranging a work bench comprising at least one spindle 14.

B. Repeatedly wrapping said at least one first threadlike element 8 around said at least one spindle 14, to form the armor 9 of said first layer 5.

C. Dissociating the armor 9 of said first layer 5 from said at least one spindle 14. This step can be carried out, for example, by elastically deforming the armor 9.

D. Repeatedly wrapping said at least one second threadlike element 38 around said at least one spindle 14, to form the armor 9 of said second layer 6. According to an embodiment, the spindle 14 used to interlace the armor 9 of said second layer 6 has a smaller caliper than the spindle used to form the armor 9 of said first layer 5, although it may be, for example, the same spindle 14 with caliber adaptation capability, for example by removing an over-spindle.

E. Dissociating the armor 9 of said second layer 6 from said at least one spindle 14. This step can be carried out by elastically deforming the armor 9

F. Fitting the armor 9 of said first layer 5 on the armor of said second layer 6.

According to a possible mode of operation, before step C. it is possible to provide a heat treatment to make the armor 9 of said first layer 5 acquire a memory of the shape in which it is on the spindle.

According to a possible mode of operation, before step E. it is possible to provide a heat treatment to ensure that the armor 9 of said second layer 6 acquires a memory of the shape in which it is on the spindle.

According to a possible mode of operation, said method provides for the step of repeating steps B to F for a third layer 7.

According to a possible mode of operation, said step F comprises at least one, but also all, of the following substeps.

G. By means of a release device 31, or deployment device, the armor 9 of said first layer 5 in a support device 32 having support walls suitable for making at least partially, but for example entirely, the armor 9 of said first layer 5 adhere. According to an embodiment, said support device 32 is an openable support device comprising reversible closing means 45. For example, said support device 32 is a sleeve which delimits a device cavity favorably shaped to replicate the shape of the armor of a layer 5, 6, 7, so as to facilitate the extraction of the armors of two or more layers 5, 6, 7 from the support device cavity. According to an embodiment, said support device 32 is substantially cup-shaped and comprises a bottom wall 36 provided with a centering hole 40 suitable for receiving a portion of the guiding element 41 of the release device 31, to provide certainty of radial positioning of the release device 31 within the support device 32. According to an embodiment, said guide element 41 comprises a stop portion 37, having a larger caliber than the centering hole 40 to provide certainty of longitudinal positioning of the release device 31 within the support device 32. According to a further step, releasing the armor 9 of said first layer 5 in said support device 32.

H. Conveying by means of a release device 31 the armor 9 of said second layer 6 in said support device 32 in which the armor 9 of said first layer 5 has been received.

According to a further step, releasing the armor 9 of said second layer 6 in said support device 32 where said armor of said first layer 5 is already present.

I. Adjusting, for example by means of an adjustment device 33, for example optical, the relative position of the threadlike elements 8, 38 of the armors 9 of said first layer 5 and of said second layer 6, before their release into said support device 32. For example, said adjustment device 33 comprises a graduated element 34 provided on said support device 32 which cooperates with an indicator 35 provided on said release device 31. For example, said step I allows the armors 9 of two adjacent layers 5, 6, 7 to be angularly or circumferentially offset by a predetermined angular quantity.

J. Connecting together, according to an embodiment but not necessarily crimping, at least a stretch, for example in the connecting portion between the at least one working portion 12 and the at least one anchoring portions 10, of said at least one threadlike element 8 of the armor 9 of said first layer 5 with the at least one threadlike element 8 of the armor 9 of said second layer 6, to form at least one anchoring portion 10. According to an embodiment but not necessarily, this step is carried out by using a crimping tool 39.

According to a possible mode of operation, said step J is carried out by opening said support device 32 and extracting the at least two mutually associated layers. According to an embodiment, the extraction of the at least two mutually associated layers is carried out after having fitted and temporarily fixed said at least two layers on an expandable element 38, for example a balloon for stents, associated with a release device 31.

According to an embodiment, said step B is carried out by using at least one return and winding device 42 movable with respect to said spindle 14 and associated with said at least one threadlike element 8, 38, 48. For example, said return and winding device 42 is a shuttle adapted to move at least longitudinally and circumferentially with respect to said spindle 14. According to an embodiment, said return and winding device 42 comprises at least two separate shuttles movable independently of one another and movable at least longitudinally and circumferentially with respect to said spindle 14. According to an embodiment, said spindle 14 is a movable element, for example suitable for rotating about the longitudinal axis thereof. According to an embodiment, said return and winding device 42 is integrally associated with a support structure 46 movable with respect to said spindle 14.

According to an embodiment, said step B is carried out by winding two opposite ends 28, 29 of a single threadlike element 8, 38, 48, to form an interleaved armor 9.

According to an embodiment, said step B is carried out by winding two opposite ends 28, 29 of a single threadlike element 8, 38, 48 in a circumferentially opposite direction, to form an interleaved armor 9 which forms a weft-warp type fabric.

According to an embodiment, said spindle 14 comprises a spindle stem 43, for example in a dog bone shape, from which return fingers 44 project cantilevering, suitable for acting as return elements for said at least one threadlike element 8, 38, 48, during at least step B and/or step D.

By such a method, it is possible to fit said two or more layers on each other in a predictable and precise manner, and it is possible to implement a luminal endoprosthesis 1 having two or more coaxial layers.

Those skilled in the art may make several adjustments and replacements of elements with others which are functionally equivalent to the embodiments described above in order to meet incidental and specific needs, without departing from the scope of the following claims.

According to an embodiment, a luminal endoprosthesis assembly 1 delimits at least partially a prosthesis lumen 2. This endoprosthesis assembly is suitable for an implant in an anatomical structure 3 which at least partially defines at least one cavity 4 and comprises at least one treatment portion 13.

According to an embodiment, said luminal endoprosthesis assembly 1 comprises at least three layers 5, 6, 7, arranged coaxially and having, in undeformed conditions, a prevalent extension along a longitudinal direction X-X and defining a radial direction R-R orthogonal to said longitudinal direction X-X and an annular or substantially circumferential direction C-C orthogonal to said longitudinal X-X and radial R-R directions.

According to an embodiment, each layer 5 or 6 or 7, in an undeformed condition, is substantially entirely superimposed on the adjacent layers 5, 6, 7.

According to an embodiment, each layer 5 or 6 or 7 of said three layers 5, 6, 7 comprises at least one threadlike element 8 forming an interleaved armor 9 limited to said at least one layer 5 or 6 or 7.

According to an embodiment, said luminal endoprosthesis 1 comprises at least one working portion 12, suitable for facing at least the treatment portion 13 of the anatomical structure 3.

According to an embodiment, said luminal endoprosthesis 1 comprises at least one anchoring portion 10, suitable for anchoring to anatomical portions 11 of the walls of the cavity 4 of the anatomical structure.

According to an embodiment, said at least three layers 5, 6, 7 are geometrically identical to each other.

According to an embodiment, said at least three layers 5, 6, 7 are separated from each other at least in said working portion 12, of the luminal endoprosthesis assembly 1, thus avoiding to provide connecting elements between one layer 5 or 6 or 7 and at least one adjacent layer.

According to an embodiment, said at least one working portion 12 only includes said at least one threadlike element 8 which forms said armor 9 with its interlacement, or interleaving, which remains only inside the same layer 5 or 6 or 7 avoiding to connect adjacent layers.

According to an embodiment, said working portion 12 of each layer 5 or 6 or 7, with the exception of a possible support thereof in the radial direction R-R to the adjacent layers 5 or 6 or 7, when the assembly is in undeformed condition, is structurally and geometrically separated from the adjacent layers 5 or 6 or 7, so as to be free to move with respect to the adjacent layers 5 or 6 or 7.

According to an embodiment, said at least one threadlike element 8, 38, 48 of the armor 9 of each layer 5, 6, 7 defines a plurality of windows 15 suitable for putting the prosthesis lumen 2 in fluidic communication with the treatment portion 13 of the anatomical structure 3.

According to an embodiment, said at least one working portion 12 of each layer 5, 6, 7, when in an undeformed condition, has said plurality of windows 15 substantially identical to each other and identical to each other in all the layers 5, 6, 7.

According to an embodiment, said at least one working portion 12 of each layer 5, 6, 7, when in undeformed conditions, has an extension in radial direction R-R or transverse to said longitudinal direction X-X, or diameter D1, D2, D3, smaller than the extension transverse to said longitudinal direction X-X, or diameter D4, of the at least one anchoring portion 10.

According to an embodiment, said at least three layers 5, 6, 7, when in undeformed conditions, are mutually offset from each other along said circumferential direction C-C around said longitudinal direction X-X.

According to an embodiment, at least one of said anchoring portions 10 of each layer 5, 6, 7 is connected to the adjacent anchoring portion 10 of the adjacent layer 5, 6, 7.

Due to the above-mentioned embodiments, blood stream regularization is induced within the aneurysm zone, producing immediately after implantation the reduction of stress on the aneurysmal wall and, in the medium-long term, the remodeling of the aneurysmal wall itself.

According to an embodiment, said at least one working portion 12 of each layer 5, 6, 7 has said plurality of windows 15. Said plurality of windows 15 are, when said assembly is in an undeformed condition, identical in shape and size in each layer of said layers 5, 6, 7.

According to an embodiment, said at least three layers 5, 6, 7, when in undeformed conditions, are also identical in their transversal dimensions D1=D2=D3, along said radial direction R-R, resulting when fitted one into the other, substantially resting against each other and avoiding a substantial radially directed action R-R if not that of support, and therefore substantially free to move at least along said longitudinal and circumferential directions X-X; C-C with respect to each other.

According to an embodiment, at least one of said at least three layers 5, 6, 7, when in undeformed conditions, has a section transverse to its longitudinal direction X-X of non-circular shape 47.

According to an embodiment, at least one of said at least three layers 5, 6, 7, when in undeformed conditions, has a section transverse to its longitudinal direction X-X of an ellipse or lenticular shape, or trilobed 49, or quadrilobed so as to maintain portions of its circumferential extension C-C separated and detached from at least one adjacent layer 5, 6, 7.

According to an embodiment, said at least one layer of said at least three layers 5, 6, 7 which, when in undeformed conditions, has a section transverse to its longitudinal direction X-X of non-circular shape, has its cross-section which changes its angular orientation, or angular phasing, along the longitudinal extension X_X of the layer, defining precisely the clearance present between each layer along its whole longitudinal extension X-X or at least along the longitudinal extension X-X of its working portion 12.

According to an embodiment, at least one of said at least three layers 5, 6, 7, when in undeformed conditions, has a section transverse to its longitudinal direction X-X of variable dimensions along the longitudinal extension X-X of said layer 5, 6, 7.

According to an embodiment, said at least three layers 5, 6, 7, when in undeformed conditions, are aligned angularly along said circumferential direction C-C aligning the plurality of windows suitable for putting the prosthesis lumen into fluidic communication 2 with the treatment portion 13 of the anatomical structure 3, so that under deformed conditions of the assembly implanted in the vessel to be treated, the windows are offset between each layer, ensuring the desired porosity of the assembly.

According to an embodiment, said threadlike element 8 has a circular section transverse to its longitudinal extension 50.

According to an embodiment, said threadlike element 8 has an elliptical section transverse to its longitudinal extension 51; or elliptic section 51 with a diagonal of the ellipse directed substantially in the circumferential direction C-C of the assembly; or square section 52; or rectangular section 53; or rectangular section 53 with the longer side of the rectangle directed substantially in the circumferential direction C-C of the assembly; or polynomial section, for example hexagonal 54.

According to an embodiment, said threadlike element 8 has a multilayer body, in which each layer is made of a different material.

According to an embodiment, said threadlike element 8 has a multilayer body, in which the innermost layer, or core, is made of metallic material 55, for example made of superelastic material, for example of Nitinol®, and the outermost layer 56 is of a different material, for example made of bioabsorbable or bio-erodible material.

According to an embodiment, said threadlike element 8 comprises at least one portion thereof of Nitinol®.

According to an embodiment, said threadlike element 8 comprises at least one portion thereof of a chromium-cobalt alloy.

According to an embodiment, said threadlike element 8 comprises at least one portion thereof of MP35N.

According to an embodiment, said threadlike element 8 comprises at least one portion thereof of Elgiloy®.

According to an embodiment, said threadlike element 8 comprises at least one portion thereof of a polymeric material.

According to an embodiment, said threadlike element 8 comprises at least one portion thereof of a bio-erodible polymeric material.

According to an embodiment, said threadlike element 8 comprises at least one portion thereof of a bio-erodible polymeric material loaded with a drug, for example one or more drugs dispersed in polymeric matrices.

According to an embodiment, said armor 9 interleaved with a threadlike element 8 has a weft and warp interleaving pattern obtained with a thread and simple interleaving with passage of each thread 8 over and then under the threads which said threadlike element 8 crosses, along said threadlike element 8.

According to an embodiment, said armor 9 interleaved with a threadlike element 8 has a weft and warp interleaving pattern obtained with a single thread and simple interleaving with passage of each thread 8 above and then below the threads which said threadlike element 8 crosses, along said threadlike element 8.

According to an embodiment, said armor 9 interleaved with a threadlike element 8 has a weft and warp interleaving pattern obtained with a thread and interleaving with passage of each thread 8 twice over and then twice under the threads which are crossed along said thread 8.

According to an embodiment, said armor 9 interleaved with a threadlike element 8 has a weft and warp interleaving pattern obtained with a first thread 8 interleaved with a second thread 57 having a section larger than the first thread.

According to an embodiment, said armor 9 interleaved with a threadlike element 8 has a weft and warp interleaving pattern obtained with a first thread 8 interleaved with a second thread 57, where said second thread 58 comprises at least one portion thereof of bioerodible material.

According to an embodiment, said armor 9 interleaved with a threadlike element 8 has a weft and warp interleaving pattern obtained with a first thread 8 interleaved with a constant interleaving angle of the thread stretches, when said assembly is in undeformed condition.

According to an embodiment, said armor 9 interleaved with a threadlike element 8 has a weft and warp interleaving pattern obtained with at least one thread 8 interleaved with a constant interleaving angle of the thread stretches by 45° with respect to the circumferential direction C-C, when said assembly is in undeformed conditions.

According to an embodiment, said armor 9 interleaved with a threadlike element 8 has a weft and warp interleaving pattern obtained with at least one thread 8 interleaved with a constant interleaving angle of the thread stretches smaller than 45° with respect to the circumferential direction C-C, when said assembly is in undeformed conditions.

According to an embodiment, said armor 9 interleaved with a threadlike element 8 has a weft and warp interleaving pattern obtained with at least one thread 8 interleaved with a constant interleaving angle of the thread stretches greater than 45° with respect to the circumferential direction C-C, when said assembly is in undeformed conditions.

According to an embodiment, said armor 9 interleaved with a threadlike element 8 has a weft and warp interleaving pattern obtained with at least one interleaved thread 8, forming a plurality of windows 15 having a predefined width in a direction parallel to the longitudinal direction X-X of 3 mm, in undeformed conditions of the assembly.

According to an embodiment, said assembly of said at least three layers 5, 6, 7 each comprising said armor 9 interleaved with a threadlike element 8, having a weft and warp interleaving pattern obtained with at least one interleaved thread 8, forms a plurality of windows 15 which, when the three layers are superimposed and in undeformed conditions, form superimposed windows having an overall free width of assembly in a direction parallel to the longitudinal direction X-X of 1 mm.

According to an embodiment, said assembly of layers 5, 6, 7 each comprising said armor 9 interleaved with a threadlike element 8, having a weft and warp interleaving pattern obtained with at least one interleaved thread 8, forms a plurality of windows 15 which, when the layers are superimposed and in undeformed conditions, form superimposed windows having overall free width of assembly in a direction parallel to the predefined longitudinal direction X-X; where in the single layer 5, 6, 7, the number of windows 15 of the single layer is given by the following relationships:

$$Ncl = \pi \Phi / Nl \times Dc \text{ and}$$

$$Sl = 360 / Ncl \times Nl$$

where
Ncl: number of windows 15 of the single layer 5, 6, 7
Φ: diameter of the working portion 12 of the assembly
Nl: number of layers 5, 6, 7 forming the assembly
Dc: diagonal of the window resulting from the overlap superposition and angular offset of the layers
Sl: angular offset between the layers in the assembly.

According to an embodiment, said armor 9 interleaved with a threadlike element 8 has a weft and warp interleaving pattern obtained with at least one interleaved thread 8, said interleaving is obtained, in at least some interleaving, by pulling or tensioning thread 8 during weaving.

According to an embodiment, at least one layer of said layers 5, 6, 7 comprises a first telescopic layer portion 59 housed in a second telescopic layer portion 60 mutually movable in a longitudinal direction X-X.

According to an embodiment, the thread used for making a layer is characterized by a circular section. Various types of sections other than the circular one can be configured to provide the layers, or some of them, with particular features, such as: greater radial or axial rigidity; greater coverage of the vessel surface or interface with the aneurysm; specific fluid dynamic effects.

According to an embodiment, the characterizing element of the thread is the material of which it is made. A preferred solution provides the use of a Nitinol® thread. The following may be considered as alternative materials: other highly elastic metal alloys (CoCr alloys, MP35N, Elgiloy®, etc.), polymers, bioerodible polymers or bioerodible polymers loaded with drugs.

The layers can be made with threads of different materials, to obtain particular functional performances. In particular, the introduction of bioerodible polymer threads for making one or more layers, or of a part of the layer, allows to have assemblies provided with a variable porosity over time. From this point of view, a particularly interesting shape for making the thread is that which provides, for example, a metal core coated with a bioerodible polymer.

According to an embodiment, the adoption of drugs dispersed in polymeric matrices would allow to implement diversified and customized therapeutic solutions.

According to an embodiment, the interleaving of the threads in the preferred embodiment is characterized by a simple weft-warp interleaving pattern, obtained with a single thread, and with 45° crossings with respect to the longitudinal axis of the assembly. The interleaving of the threads and its features are fundamental elements for defining the porosity and conformability, in a broad sense, of the device. The possible variation factors identified are:
  the weaving scheme and/or
  the diameter and the shape of the interleaved threads and/or
  the materials of the woven threads and/or
  the crossing angle of the interleaved threads and/or
  the tensioning of the interleaved threads and/or
  the mix of two or more of the aforesaid factors.

According to an embodiment, the interleaving pattern adopted in the formation of the layers can confer to the assembly, with the same diameter and material of the threads, specific mechanical features, in particular as regards the conformability and the possibility for the threads of performing micro-movements when exposed to the blood stream. These two features can be obtained in an isotropic or anisotropic way, always playing on the interleaving patterns.

According to an embodiment, the use of threads of different diameters and/or shapes can result in layers of specific conformability and specific porosity. These embodiments differ in the choice of having a single thread that forms the entire layer.

According to an embodiment, solutions are adopted in which metal threads variably alternating are interleaved with threads of bioerodible polymer to obtain low initial porosities, intended to increase with the dissolving of the polymer meshes.

According to an embodiment, another design lever for varying the isotropic and/or anisotropic porosity and conformability is represented by the interleaving angles of the threads. Winding angles with respect to the longitudinal axis of the assembly which are very large or very small will provide low porosities (other factors being equal). Small winding angles will provide low radial resistance, conversely for large winding angles.

According to an embodiment, the tensioning imparted to the threads at the time of weaving allows to obtain layers with more tensioned threads characterized by lower conformability and possibility of movement for the threads.

According to an embodiment, the great design flexibility is given by the mix of the interleaving variants listed above. Two examples of particular interest are given by solutions with a variable angle interleaving, for radially more rigid ends and a more conformable working part, or with the creation of a central area with low porosity at the aneurysmal part (possibly using biodegradable threads).

According to an embodiment, the preferred design of the assembly provides for the use of 3 equal layers, equally offset from each other in a circumferential angular direction.

According to an embodiment, a fundamental parameter of the device is the measurement of the diagonal Dc of the single window or cell of the assembly or stent, as a result of the superposition of a plurality of equal layers. This diagonal Dc is important because it measures the porosity of the device. It basically represents the preferable porosity of the assembly.

According to an embodiment, the same value of diagonal Dc can be obtained by superimposing many layers consisting of single windows or large cells, or a few layers made up of individual small cells. The fundamental relationships that regulate these geometries are the following:

number of cells of the single layer:

$$Ncl=\pi\Phi/(Nl \times Dc)$$

angular offset between layers in the complete device:

$$Sl=360/(Ncl \times Nl)$$

where:
Ncl: number of cells of the single layer;
Φ: diameter of the working part of the complete stent;
Nl: number of layers forming the complete stent;
Dc: diagonal of the cell resulting from the superposition and offset of the layers;
Sl: angular offset between layers in the complete device.

According to an embodiment, Dc is 1 mm; Nl is 3; Φ is 20 mm; then Ncl=20 and Sl=6°

The same value of Dc can be obtained with 4 layers, but having Ncl=16 and Sl=5.6°

Achieving the same final porosity value Dc with many layers of loose meshes rather than few with thicker meshes can give the stent a greater conformability and possibility of movement for the individual threads but increasing the risk of inhomogeneity in tortuous areas.

Another variant to the design obtainable playing on the layers is represented by the possibility of creating, along the axis, zones with more or less layers.

According to an embodiment, the use of different layers according to the thickness of the mesh, the diameter and shape of the thread, the material of the thread, the winding angle of the thread, allows a considerable flexibility of production. These variations allow to obtain many nuances of performances in terms of mechanical behavior and conformability.

In this perspective, the possibility of introducing bioerodible polymer layers to give the stent a variable porosity over time, appears to be of particular interest.

According to an embodiment, the individual layers can be connected to each other by crimped bushings, as in the basic design, or by crimped bands, welds, ties, dedicated anchoring systems.

According to an embodiment, the number of connection points can be varied: more "linked" layers result in stiffer, more flexibly rigid, less conformable stents, with less mobility of the threads but more precise and homogeneous in terms of porosity. The effects of the connection can be suitably distributed depending on the functionality to be achieved.

An interesting implementation option based on the interconnection pattern between layers can be as follows. If the various layers are connected to each other, as in the preferred design, only at the ends and without oversizing with respect to each other, the layers in the working area will have a certain degree of relative circumferential freedom. This freedom will give rise to a local alteration of the resulting porosity, especially in situations of tortuous or in any case winding implant conditions. In particular, again in the basic design which provides three offset layers so as to obtain at least a minimum initial resulting porosity, the alteration caused by curves and tortuosities will lead to unavoidably higher local porosity with respect to the undeformed condition (wider meshes). Overturning this observation, that is, keeping the connection between layers at the ends only, but with perfectly phased layers, there will be an initial undeformed condition with large mesh. In tortuous or winding conditions, the resulting relative movement between layers will inevitably produce smaller resulting meshes, i.e. lower porosities. Such a device can be useful for devices intended for curved implantation, with aneurysm to the extrados, because the porosity of the area facing the aneurysm itself will be lower than the original one, and therefore capable of enhancing the desired flow laminarization effect.

In the preferred design, the three layers are "gently in contact" with each other, that is, they touch each other without a significant exchange of radial forces. By playing with the differences in diameter between layers, it is possible to confer specific functions to the stent as a whole: layers that touch with significant radial force exchange will produce stiffer, less conformable stents, and with less possibility of micro-movements of the individual threads under the action of the blood stream; conversely with non-touching layers. Some of the variants that can be devised are represented herein.

The layers can be separated from one another only by virtue of the difference in diameter, or by separators.

A solution of particular interest for having separate layers, at a stable and controlled distance, without using separators, consists in providing one or more layers of polygonal shapes. For example, in a three-layer version, the central one has a vaguely triangular shape. By playing with the magnitude of this triangularization, different distances can be obtained between the outer and inner layers. Other polygonal shapes can also serve the purpose.

The generatrixes in contact between the layers can be rectilinear, that is, parallel to the axis of the stent, or follow specific shapes, for example a helix, to give particular trajectories to the intra-layer blood stream.

The axial shape of the layers can also be subjected to variations in order to obtain specific functionalities, for example with progressive curvature to avoid the "dog bone" effect at the ends, following the implantation, or an intermediate curved layer to create special fluidic effects.

The preferred design provides a stent which, although made up of layers, is monolithic as a whole. It is possible to imagine a solution with two telescopic stents for implant to achieve the optimal coverage of long lesions.

With the solutions described above, the luminal endoprosthesis assembly allows multiple clinical applications:
a) treatment of aneurysms in aortic stretches;
b) treatment of aneurysms in peripheral vessels;
c) treatment of aortic dissections.

REFERENCE LIST

1 Luminal endoprosthesis
2 Prosthetic lumen
3 Anatomical structure
4 Anatomical structure cavity
5 First layer
6 Second layer
7 Third layer 8 Threadlike element, or first threadlike element
9 Armor
10 Anchoring portion of the endoprosthesis
11 Anatomical portion of the anatomical structure
12 Working portion of the endoprosthesis
13 Pathological portion of the anatomical structure
14 Spindle
15 Windows
16 Space between adjacent layers
17 Aneurysm
18 Aortic arch
19 Descending aorta
20 Thoracic aorta
21 Abdominal aorta
22 Aortic isthmus
23 Collateral vessels
24 Layer connection device, or connection element
25 End connection device, or connection element
26 Proximal endoprosthesis end
27 Distal endoprosthesis end
28 First threadlike element end
29 Second threadlike element end
30 Crossing site
31 Release device
32 Support device
33 Adjustment device
34 Graduated element of the adjustment device
35 Indicator of the adjustment device
36 Bottom wall of the support device
37 Stop portion
38 Second threadlike element
39 Crimping tool
40 Centering hole
41 Guiding element of the adjustment device
42 Return and winding device
43 Spindle stem
44 Spindle fingers
45 Reversible closing means
46 Support structure
47 Circular cross-section at the longitudinal extension of the single layer
48 Third threadlike element
49 Trilobed cross-section at the longitudinal extension of the single layer
50 Circular cross-section of the thread
51 Elliptical cross-section of the thread
52 Square cross-section of the thread
53 Rectangular cross-section of the thread
54 Hexagonal cross-section of the thread
55 Metallic core of the thread
56 Outer layer of the threads of bioerodible material
57 Second thread larger than the first thread
58 Second thread of bioerodible material
59 First telescopic layer portion
60 Second telescopic layer portion
61 Stent delivery system
62 First release sheath
63 Second release sheath
Ncl Number of windows of the single layer
Φ diameter of the working portion of the assembly
Nl number of layers forming the assembly
Dc diagonal of the window resulting from the overlap superposition and angular offset of the layers
Sl angular offset between the layers in the assembly
D1 First layer caliber or nominal diameter
D2 Second layer caliber or nominal diameter
D3 third layer caliber or nominal diameter
D4 Caliber or nominal diameter of the anchoring portion
X-X Longitudinal direction
R-R Radial direction
C-C Circumferential direction
RE External radial direction

The invention claimed is:

1. A luminal endoprosthesis assembly at least partially delimiting a prosthesis lumen, for an implant in an anatomical structure which at least partially defines a cavity and comprises a treatment portion, said luminal endoprosthesis assembly comprising:

three or more layers, arranged coaxially and having, in an undeformed condition, a prevalent extension along a longitudinal direction and defining a radial direction orthogonal to said longitudinal direction and an annular or circumferential direction orthogonal to said longitudinal and radial directions; the three or more layers defining in part:

at least one working portion, for facing at least the treatment portion of the anatomical structure, and at least two anchoring portions, longitudinally opposite with respect to said at least one working portion and for being anchored to anatomical portions of walls of the cavity of the anatomical structure;

Wherein:

said three or more layers are separated from each other, at least in said at least one working portion, of the luminal endoprosthesis assembly, thus avoiding connecting elements between one layer of the three or more layers and at least one adjacent layer of the three or more layers;

said each layer of said three or more layers comprises at least one threadlike element forming armor with interleaving which remains only inside a same layer of each of the three or more layers and limitedly interlaced to said same layer of said three or more layers and within the at least one working portion avoiding connecting adjacent layers of the three or more layers and avoiding other fabrics or structures or grafts;

said at least one working portion, with the exception of a possible support in a radial direction to the adjacent layers, when the assembly is in the undeformed condition, is structurally and geometrically separated from the adjacent layers to be free to move with respect to the adjacent layers;

at least one filiform or said at least one threadlike element of the armor of each layer of the three or more layers defines a plurality of windows for putting the prosthesis lumen in fluidic communication with the treatment portion of the anatomical structure;

said at least one working portion, when in the undeformed condition, has said plurality of windows substantially identical to each other and identical to each other in all the layers;

said at least one working portion, when in the undeformed condition, has an extension in the radial direction or transverse to said longitudinal direction, or diameter, smaller than an extension transverse to said longitudinal direction, or diameter, of the at least two anchoring portions;

at least one of the three or more layers in at least one of said at least two anchoring portions is connected to at least one adjacent layer of the three or more layers;

said each layer of said three or more layers, in the undeformed condition, is entirely superimposed on adjacent layers;

said three or more layers are geometrically and structurally identical to each other; and said three or more layers, when in the undeformed condition, are mutually offset from each other along said circumferential direction around said longitudinal direction.

2. A luminal endoprosthesis assembly according to claim 1, having a shape as a dog bone, comprising opposite ends larger than a portion of the luminal endoprosthesis longitudinally interposed between said two opposite ends; and/or wherein said at least two anchoring portions are larger than said at least one working portion.

3. A luminal endoprosthesis assembly according to claim 1, wherein said at least two anchoring portions comprise at least one connecting device between said three or more layers.

4. A luminal endoprosthesis assembly according to claim 1, wherein each layer of said three or more layers comprises a single threadlike element of the at least one threadlike element.

5. A luminal endoprosthesis assembly according to claim 1, wherein said three or more layers, in said at least one working portion, are mutually spaced by a predetermined distance, said distance between the layers is equal to or greater than a distance that prevents endothelial cells from adhering, thereby connecting the layers, preventing said endothelial cells from forming a bridge-like connection between the layers, for preventing a compaction of the layers, and wherein said distance between the adjacent layers forms a space which extends without interruption at least along all of the at least one working portion of the endoprosthesis.

6. A luminal endoprosthesis assembly according to claim 1, wherein said three or more layers are coaxial; and/or wherein said three or more layers comprise a first layer having a predetermined nominal caliber of the first layer, a second layer having a predetermined nominal caliber of the second layer smaller than said nominal caliber of the first layer, and a third layer, having a predetermined nominal caliber of the third layer smaller than both said nominal caliber of the first layer and said nominal caliber of the second layer; and/or wherein said luminal endoprosthesis comprises three or more armors which form said three or more layers.

7. A luminal endoprosthesis assembly according to claim 1, wherein an end of a first threadlike element of said at least one threadlike element and an end of a second threadlike element of said at least one threadlike element form a crossing angle with respect to the longitudinal direction of the luminal endoprosthesis; and wherein said crossing angle is of between 40° and 50°.

8. A luminal endoprosthesis assembly according to claim 7, wherein said crossing angle is substantially equal to 45°.

9. A luminal endoprosthesis assembly according to claim 1, wherein the armor formed by the at least one threadlike element of one layer of the three or more layers is circumferentially offset with respect to the armor of one or more adjacent layers by a predetermined amount of offset smaller than the circumferential distance between two successive crossing sites and/or by an amount of offset smaller than one third of a circumferential distance between two successive crossing sites.

10. A luminal endoprosthesis assembly according to claim 1, wherein said at least one threadlike element is made of a super-elastic and/or shape memory material; and/or wherein said at least one threadlike element is at least partially made of nickel titanium; and/or wherein said at least one threadlike element is made of material for maintaining memory of a predefined shape and for reacquiring the predefined shape when the at least one threadlike element undergoes thermal variations and/or mechanical stresses.

11. A luminal endoprosthesis assembly according to claim 1, wherein said luminal endoprosthesis is a stent-no-graft.

12. A luminal endoprosthesis assembly according to claim 1, wherein said at least one working portion has a frusto-conical shape.

13. A luminal endoprosthesis assembly according to claim 1, wherein said luminal endoprosthesis comprises a bifurcation of the prosthesis lumen.

14. A luminal endoprosthesis assembly according to claim 1, wherein at least one of said three or more layers, when in the undeformed condition, has a section transverse to the longitudinal direction of the at least one of said three or more layers of non-circular shape; and/or wherein at least one of said three or more layers, when in the undeformed condition, has a section transverse to the longitudinal direction of an ellipse or lenticular shape, or trilobed, or quadrilobed so as to maintain portions of a circumferential extension separated and detached from at least one adjacent layer; and/or wherein said at least one layer of said three or more layers which, when in the undeformed condition, has a section transverse to the longitudinal direction of non-circular shape, has a cross-section which changes angular orientation, or angular phasing, along a longitudinal extension of the layer of the three or more layers defining precisely the clearance present between each layer of the three or more layers along the whole longitudinal extension or at least along the longitudinal extension of said at least one working portion; and/or wherein at least one of said three or more layers, when in the undeformed condition, has a section transverse to the longitudinal direction of the at least one of said three or more layers of variable dimensions along the longitudinal extension of said layer.

15. A luminal endoprosthesis assembly according to claim 14, wherein said at least one threadlike element has a circular section transverse to the longitudinal extension;

and/or wherein said at least one threadlike element has an elliptical section transverse to the longitudinal extension; or elliptic section with a diagonal of the ellipse directed in the circumferential direction of the assembly; or square section; or rectangular section; or rectangular section with a longer side of the rectangle directed in the circumferential direction of the assembly; or polygonal section.

16. A luminal endoprosthesis assembly according to claim 1, wherein said at least one threadlike element has a multilayer body, in which each layer of the multilayer body is made of a different material;

and/or wherein said at least one threadlike element has a multilayer body, in which the innermost layer of the multilayer body, or core, is made of nickel titanium, and the outermost layer of the multilayer body is bioabsorbable or bio-erodible material;

and/or wherein said at least one threadlike element comprises at least one portion of nickel titanium; and/or wherein said at least one threadlike element comprises at least one portion of a chromium-cobalt alloy; and/or wherein said at least one threadlike element comprises at least one portion of MP35N;

and/or wherein said at least one threadlike element comprises at least one portion of a non-magnetic cobalt-chromium-nickel-molybdenum alloy; and/or wherein said at least one threadlike element comprises at least one portion of a polymeric material; and/or wherein said at least one threadlike element comprises at least one portion of a bioerodible polymeric material; and/or wherein said at least one threadlike element comprises at least one portion of a bioerodible polymeric material loaded with a drug dispersed in polymeric matrices.

17. A luminal endoprosthesis assembly according to claim 1, wherein said armor interleaved with at least one threadlike element has a weft and warp interleaving pattern obtained with a thread of the at least one threadlike element and simple interleaving with passage of each thread of the at least one threadlike element over and then under threads which said at least one threadlike element crosses, along said at least one threadlike element;

and/or wherein said armor interleaved with at least one threadlike element has a weft and warp interleaving pattern obtained with a single thread of the at least one threadlike element and simple interleaving with passage of the single thread of the at least one threadlike element above and then below threads which said single thread crosses, along said single thread;

and/or wherein said armor interleaved with at least one threadlike element has a weft and warp interleaving pattern obtained with each thread of the at least one threadlike element and interleaving with passage of each thread of the at least one threadlike element twice over and then twice under threads which are crossed along said thread;

and/or wherein said armor interleaved with at least one threadlike element has a weft and warp interleaving pattern obtained with a first thread of the at least one threadlike element interleaved with a second thread of the at least one threadlike element having a section larger than the first thread of the at least one threadlike element;

and/or wherein said armor interleaved with at least one threadlike element has a weft and warp interleaving pattern obtained with a first thread of the at least one threadlike element interleaved with a second thread of the at least one threadlike element, where said second thread of the at least one threadlike element comprises at least one portion thereof of bioerodible material;

and/or wherein said armor interleaved with at least one threadlike element has a weft and warp interleaving pattern obtained with a first thread of the at least one threadlike element interleaved with a constant interleaving angle of the thread, when said assembly is in the undeformed condition;

and/or wherein said armor interleaved with at least one threadlike element has a weft and warp interleaving pattern obtained with at least one thread of the at least one threadlike element interleaved with a constant interleaving angle of the thread of the at least one threadlike element by 45° with respect to the circumferential direction, when said assembly is in the undeformed condition;

and/or wherein said armor interleaved with at least one threadlike element has a weft and warp interleaving pattern obtained with at least one thread of the at least one threadlike element interleaved with a constant interleaving angle of the thread of the at least one threadlike element smaller than 45° with respect to the circumferential direction, when said assembly is in the undeformed condition;

and/or wherein said armor interleaved with at least one threadlike element has a weft and warp interleaving pattern obtained with at least one thread of the at least one threadlike element interleaved with a constant interleaving angle of the thread of the at least one threadlike element larger than 45° with respect to the circumferential direction, when said assembly is in the undeformed condition;

and/or wherein said armor interleaved with at least one threadlike element has a weft and warp interleaving pattern obtained with at least one interleaved thread, forming a plurality of windows having a predefined width in a direction parallel to the longitudinal direction of 3 mm, in the undeformed condition of the assembly.

18. A luminal endoprosthesis assembly according to claim 1, wherein said assembly of said three or more layers each comprises said armor interleaved with at least one threadlike element, having a weft and warp interleaving pattern obtained with at least one interleaved thread, forms a plurality of windows which, when the three or more layers are superimposed and in the undeformed condition, form superimposed windows having an overall free width of assembly in a direction parallel to the longitudinal direction of 1 mm;

and/or wherein said assembly of said three or more layers each comprising said armor interleaved with at least one threadlike element, having a weft and warp interleaving pattern obtained with at least one interleaved thread, forms a plurality of windows which, when the layers of said three or more layers are superimposed and in the undeformed condition, form superimposed windows having an overall free width of assembly in a direction parallel to the predefined longitudinal direction; wherein in a single layer of the three or more layers, the number of windows of the single layer is given by the following relationships:

$Ncl=\pi\Phi/Nl \times Dc$ and $Sl=360/Ncl \times Nl$ where

Ncl: number of windows of the single layer;

Φ: diameter of the at least one working portion of the assembly;

Nl: number of layers forming the assembly;

Dc: diagonal of the window resulting from overlap superposition and angular offset of the three or more layers;

Sl: angular offset between the layers in the assembly.

19. A luminal endoprosthesis assembly according to claim 1, wherein said armor interleaved with at least one threadlike element has a weft and warp interleaving pattern obtained with at least one interleaved thread, said interleaving is obtained, in at least some interleaving, by pulling or tensioning thread of the at least one threadlike element during weaving.

* * * * *